(12) United States Patent
Agustsson et al.

(10) Patent No.: US 11,800,631 B2
(45) Date of Patent: Oct. 24, 2023

(54) MODIFIED SPLIT STRUCTURE PARTICLE ACCELERATORS

(71) Applicant: RadiaBeam Technologies, LLC, Santa Monica, CA (US)

(72) Inventors: Ronald Agustsson, Venice, CA (US); Salime Boucher, Santa Monica, CA (US); Sergey Kutsaev, Santa Monica, CA (US)

(73) Assignee: RadiaBeam Technologies, LLC, Santa Monica, CA (US)

( * ) Notice: Subject to any disclaimer, the term of this patent is extended or adjusted under 35 U.S.C. 154(b) by 0 days.

(21) Appl. No.: 17/886,212

(22) Filed: Aug. 11, 2022

(65) Prior Publication Data

US 2023/0082826 A1 Mar. 16, 2023

Related U.S. Application Data

(63) Continuation of application No. 17/276,446, filed as application No. PCT/US2019/051748 on Sep. 18, 2019, now Pat. No. 11,612,049.

(Continued)

(51) Int. Cl.
*H05H 9/02* (2006.01)
*H05H 7/18* (2006.01)
*H05H 7/22* (2006.01)

(52) U.S. Cl.
CPC .............. *H05H 9/02* (2013.01); *H05H 7/18* (2013.01); *H05H 7/22* (2013.01); *H05H 2007/225* (2013.01)

(58) Field of Classification Search
CPC .. H05H 9/02; H05H 7/18; H05H 7/22; H05H 2007/225
See application file for complete search history.

(56) References Cited

U.S. PATENT DOCUMENTS 2,945,981 A 7/1960 Karp
5,578,909 A 11/1996 Billen
(Continued)

FOREIGN PATENT DOCUMENTS

CA 2790793 1/2011
CN 202095170 U 12/2011
(Continued)

OTHER PUBLICATIONS

Benedetti et al., High Gradient Linac for Proton Therapy, Physical Review Accelerators and Beams 20 120401, Apr. 13, 2017.
(Continued)

*Primary Examiner* — Minh D A
(74) *Attorney, Agent, or Firm* — Knobbe, Martens, Olson & Bear, LLP

(57) ABSTRACT

A particle accelerator can include a first waveguide portion and a second waveguide portion. The first waveguide portion can include a first plurality of cell portions and a first iris portion that is disposed between two of the first plurality of cell portions. The first iris portion can include a first portion of an aperture such that the aperture is configured to be disposed about a beam axis. The first waveguide portion can further include a first bonding surface. The second waveguide portion can include a second plurality of cell portions and a second iris portion that is disposed between two of the second plurality of cell portions. The second iris portion can include a second portion of the aperture. The second waveguide portion can include a second bonding surface.

20 Claims, 21 Drawing Sheets

Related U.S. Application Data

(60) Provisional application No. 62/734,971, filed on Sep. 21, 2018.

(56) References Cited

U.S. PATENT DOCUMENTS

| | | | |
|---|---|---|---|
| 5,796,314 | A | 8/1998 | Tantawi et al. |
| 6,376,990 | B1 | 4/2002 | Allen et al. |
| 6,448,722 | B1 | 9/2002 | Yu et al. |
| 6,465,957 | B1 | 10/2002 | Whitham et al. |
| 6,646,383 | B2 | 11/2003 | Bertsche et al. |
| 7,046,765 | B2 | 5/2006 | Wong et al. |
| 7,400,096 | B1 | 7/2008 | Foster et al. |
| 7,411,361 | B2 | 8/2008 | Agustsson et al. |
| 7,423,381 | B2 | 9/2008 | Hanna |
| 7,764,324 | B2 | 7/2010 | Andonian et al. |
| 8,026,768 | B1 | 9/2011 | Burt et al. |
| 8,107,589 | B2 | 1/2012 | Sakurai et al. |
| 8,143,816 | B2 | 3/2012 | Clayton et al. |
| 8,148,922 | B2 | 4/2012 | Cleland et al. |
| 8,947,115 | B2 | 2/2015 | Rosenzweig et al. |
| 9,023,765 | B1 | 5/2015 | Rimmer et al. |
| 9,237,641 | B2 * | 1/2016 | Suzuki ............... H05H 7/16 |
| 9,287,598 | B2 | 3/2016 | Tantawi et al. |
| 9,386,682 | B2 | 7/2016 | Tantawi et al. |
| 9,398,681 | B2 | 7/2016 | Tantawi et al. |
| 9,640,851 | B2 | 5/2017 | Nantista et al. |
| 9,736,922 | B2 | 8/2017 | Trummer |
| 9,847,205 | B2 | 12/2017 | Sherman et al. |
| 9,867,271 | B2 | 1/2018 | Saverskiy |
| 9,913,360 | B1 | 3/2018 | Antipov et al. |
| 9,931,522 | B2 | 4/2018 | Bharadwaj et al. |
| 10,212,800 | B2 | 2/2019 | Agustsson et al. |
| 10,263,170 | B1 | 4/2019 | Brink et al. |
| 10,609,809 | B2 | 3/2020 | Agustsson et al. |
| 10,880,985 | B2 | 12/2020 | Agustsson et al. |
| 10,932,354 | B2 * | 2/2021 | Agustsson ............... H05H 9/00 |
| 2005/0057198 | A1 * | 3/2005 | Hanna ............... H05H 7/18 |
| | | | 315/500 |
| 2006/0115323 | A1 | 6/2006 | Coppeta et al. |
| 2006/0255991 | A1 | 11/2006 | De Abreu et al. |
| 2007/0040113 | A1 | 2/2007 | Monroe et al. |
| 2007/0086569 | A1 | 4/2007 | Johnsen |
| 2010/0320403 | A1 | 12/2010 | Amaldi et al. |
| 2011/0216886 | A1 * | 9/2011 | Ho ............... H05H 9/02 |
| | | | 315/505 |
| 2011/0290379 | A1 | 12/2011 | Murokh et al. |
| 2012/0294423 | A1 | 11/2012 | Cheung et al. |
| 2012/0319085 | A1 | 12/2012 | Gambetta et al. |
| 2013/0088224 | A1 | 4/2013 | Koizumi |
| 2013/0163707 | A1 | 6/2013 | Habs et al. |
| 2014/0119496 | A1 | 5/2014 | Zhou et al. |
| 2014/0191654 | A1 | 7/2014 | Tantawi et al. |
| 2014/0333395 | A1 | 11/2014 | Tantawi et al. |
| 2015/0057484 | A1 | 2/2015 | Amaldi |
| 2015/0194720 | A1 | 7/2015 | Tantawi |
| 2015/0338545 | A1 | 11/2015 | Arodzero et al. |
| 2015/0340752 | A1 | 11/2015 | Nantista et al. |
| 2015/0359080 | A1 | 12/2015 | Dolgashev |
| 2016/0102631 | A1 | 4/2016 | Lynn |
| 2016/0193481 | A1 | 7/2016 | Tantawi et al. |
| 2016/0310764 | A1 | 10/2016 | Bharadwaj et al. |
| 2017/0094770 | A1 | 3/2017 | Kephart |
| 2017/0325326 | A1 | 11/2017 | Tantawi et al. |
| 2017/0367171 | A1 | 12/2017 | Tantawi et al. |
| 2018/0014151 | A1 | 1/2018 | Kratz et al. |
| 2018/0073065 | A1 | 3/2018 | Bowen et al. |
| 2018/0343733 | A1 | 11/2018 | Mustapha et al. |
| 2020/0068699 | A1 | 2/2020 | Kutsaev et al. |
| 2021/0060358 | A1 | 3/2021 | Tantawi et al. |
| 2021/0204389 | A1 | 7/2021 | Agustsson et al. |
| 2021/0219413 | A1 | 7/2021 | Agustsson et al. |
| 2021/0398768 | A1 | 12/2021 | Graves et al. |
| 2022/0115758 | A1 | 4/2022 | Franzi et al. |

FOREIGN PATENT DOCUMENTS

| | | | |
|---|---|---|---|
| CN | 105555009 A | 5/2016 | |
| EP | 2421006 | 2/2012 | |
| EP | 2516006 | 3/2014 | |
| EP | 2823501 | 5/2019 | |
| JP | H04-190599 | 7/1992 | |
| RU | 2012140348 | 3/2014 | |
| WO | WO 1997/041614 | 11/1997 | |
| WO | WO 1997/041615 | 11/1997 | |
| WO | WO 2013/126120 | 8/2013 | |
| WO | WO-2016083788 A1 * | 6/2016 | ............. H05H 13/10 |
| WO | WO 2016/138395 | 9/2016 | |
| WO | WO 2018/175804 | 9/2018 | |
| WO | WO 2018/204714 | 11/2018 | |
| WO | WO 2018/222839 | 12/2018 | |
| WO | WO 2020/061204 | 3/2020 | |
| WO | WO 2020/219578 | 10/2020 | |
| WO | WO 2020/219586 | 10/2020 | |
| WO | WO 2021/113323 | 6/2021 | |

OTHER PUBLICATIONS

Cowley, Cyberknife 6D Robotic Radiosurgery Presentation, stored on Mar. 17, 2017.

Hoag, et al., Accelerator Structure Development for NLC (Work supported by Department of Energy Contracts DE-AC03-76SF00515 (SLAC), IEEE, 1993, pp. 907-909.

Kutsaev, et al., A dual-energy linac cargo inspection system, Instruments and Experimental Techniques, 2011, vol. 54, No. 2, pp. 241-248.

Kutsaev, A New Thermionic RF Electtron Gun for Synchrotron Light Sources, in 4 pages.

Kutsaev, Beam Dynamics Studies for a Compact Carbon Ion Linac for Therapy, pp. 947-949.

Kutsaev, Sergey V., High Gradient S-band Accelerating Structure for Hadron Therapy Linac, Jun. 7, 2016, Radiabeam Systems, pp. 1-23.

Kutsaev, Hellweg2D code for design of high average power traveling wave linacs, Accelerator Seminar at SLAC National Accelerator Laboratory, Sep. 1, 2016 in 28 pages.

Kutsaev, et al. High Gradient Accelerting Structures for Carbon Therapy Linac, in 4 pages.

Kutsaev, et al., Accelerating Structure for C-Band Electron Linear Accelerator Optimization, Proceedings of LINAC08, Victoria, BC, Canada, pp. 922-924.

Kutsaev, et al., Beam optics Studies for a uranium ion micro beam, Oct. 2014, in 6 pages.

Kutsaev, et al., Compact 4kW Variable RF Power Coupler for FRIB Quarter-Wave Cavities, in 3 pages.

Kutsaev, et al., Compact Electron Linear Accelerator Relus-5 for Radiation Technology Application, Proeceedings of EPAC 2006, Edinburgh, Scotland, in 3 pages.

Kutsaev, et al. , Electron Accelerators for Novel Cargo Inspection Methods, ScienceDirect, Physics Procedia 90 (2017) 115-125.

Kutsaev, et al., High Gradient Superconducting Cavity Development for FFAG, Sep. 2013, in 3 pages.

Kutsaev, et al., High Power RF Coupler for ADS Accelerating Cavities, Proceedings of SRF2013, Paris France, pp. 1050-1052.

Kutsaev, et al., High-gradient low-accelerating structure using the first negative spatial harmonic of the fundamental mode, Physical Review Special Topics—Accelerators and Beams, Dec. 2007, in 17 pages.

Kutsaev, et al., Hybrid Electron Linac Based on Magnetic Coupled Accelerating Structure, Applications of Accelerators, Tech Transfer, Industry Accel/Storage Rings 08: Linear Accelerators, pp. 2136-2138.

Kutsaev, et al., Improved charge breeding efficiency of light ions with an electron cyclotron resonance ion sourcem AIP Reivew of Scientifc Instruments 83, 2012 American Institute of Physics.

Kutsaev, et al., Input Couplers for the Dipole Mode Peridic Structures, Proceedings of RuPAC-2010, Protvino, Russia, pp. 328-331.

Kutsaev, et al., Magnetic Coupled Disk-Loaded Waveguide, Proceedings of RuPAC-2010, Protvino, Russia, pp. 319-321.

(56) References Cited

OTHER PUBLICATIONS

Kutsaev, et al.,Multipactor Simulations in Axisymmetric and Non-Axisymmetric Radio Frequency Structures, Proceedings of RuPAC 2008, Zvenigarad, Russia, pp. 215-217.
Kutsaev, et al. , Single-Shot THZ Spectrometer For Bunch Length Measurements, Logicware, Inc. New York, in 3 pages.
Kutsaev, et al., Upgrade of Argonne's CW SC Heavy Ion Accelerator, Proceedings of PAC2013, Pasadena, CA, pp. 737-739.
Kutsaev, Single-shot mm-wave spectrometer for RF breakdown detection in linear accelerators, Jun. 8, 2016, in 22 pages.
Kutsaev, Sergey V., et al. Electron Linac with Deep Energy Control for Adaptive Rail Cargo Inspection System, Manuscript received Dec. 7, 2015. This work has been partially supported by the US Department of Homeland Security, Domestic Nuclear Detection Office, under competitively awarded contract/IAA HSHQDC-13-C-B0019.
Ostroumov et al., "Compact Carbon Ion LINAC", Proceeding of NA-PAC2016 Chicago, IL, Oct. 14, 2016, pp. 1-3 (Year: 2016).
Ostroumov et al., "Compact Carbon Ion LINAC", Argonne National Laboratory NAPAC—2016, pp. 1-23 (Year: 2016).
Smirnov, A.V., et al. Multi-cell disk-and-ring tapered structure for compact RF linacs, Nuclear Instruments and Methods in Physics Research A 830, 2016, pp. 294-302.
International Search Report—PCT/US2019/051748, dated Dec. 19, 2019, 2018, 8 pages.

\* cited by examiner

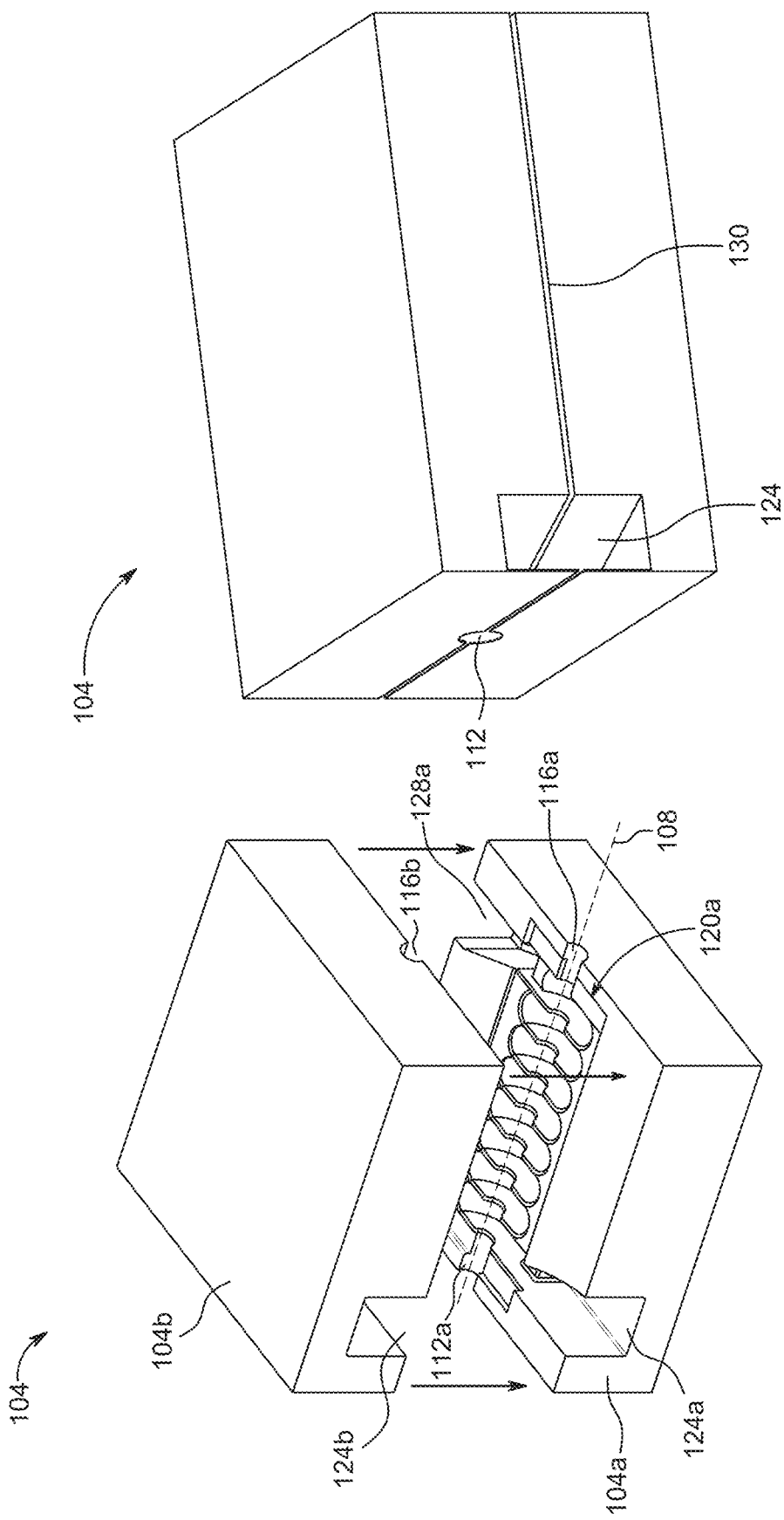

MODIFIED SPLIT STRUCTURE PARTICLE ACCELERATORS

CROSS-REFERENCE TO RELATED APPLICATIONS

This application is a continuation application of U.S. patent application Ser. No. 17/276,446, filed Mar. 15, 2021 entitled MODIFIED SPLIT STRUCTURE PARTICLE ACCELERATORS, which is the U.S. National Phase under 35 U.S.C. § 371 of International Application No. PCT/US2019/051748, filed Sep. 18, 2019, entitled MODIFIED SPLIT STRUCTURE PARTICLE ACCELERATORS, which claims the benefit of U.S. Provisional Application No. 62/734,971, filed Sep. 21, 2018, entitled "MODIFIED SPLIT STRUCTURE PARTICLE ACCELERATORS," each of which is hereby incorporated by reference herein in its entirety and for all purposes.

STATEMENT REGARDING FEDERALLY SPONSORED R&D

This invention was funded, in part, by government support under DOE Grant No. DE-SC0015722. The government has certain rights in the invention.

BACKGROUND

Field

The present disclosure relates to radiation technologies, in particular to beam generation and beam hardware.

SUMMARY

Modern radiation techniques tend to rely on bulky machinery with a limited scope of approaches for which radiation can be generated. Systems and methods disclosed herein address various challenges related to particle acceleration.

Described herein are various embodiments of linear accelerators ("linacs"), cyclic accelerators, and related components. A linac is a device commonly used for external beam radiation generation and may be used in medical treatments. As will become clear from the following disclosure, producing an effective high-gradient linac structure can present a variety of technical challenges, which may be solved by many of the novel features disclosed herein. While certain examples herein refer to a linac, those examples are equally applicable to other types of particle accelerators (e.g., cyclic accelerators).

A particle accelerator can include a first waveguide portion and a second waveguide portion. The first waveguide portion can include a first plurality of cell portions and a first iris portion that is disposed between two of the first plurality of cell portions. The first iris portion can include a first portion of an aperture such that the aperture is configured to be disposed about a beam axis. The first waveguide portion can further include a first bonding surface. The second waveguide portion can include a second plurality of cell portions and a second iris portion that is disposed between two of the second plurality of cell portions. The second iris portion can include a second portion of the aperture. The second waveguide portion can include a second bonding surface. In some embodiments, the first bonding surface is disposed adjacent the second bonding surface such that the first and second plurality of cell portions form a plurality of accelerating cells and the first and second iris portions form an iris and an aperture within the iris. Other embodiments, including structures and methods for the same, are described herein.

BRIEF DESCRIPTION OF THE DRAWINGS

Certain embodiments of the present disclosure will now be described, by way of example only, with reference to the accompanying drawings. From figure to figure, the same or similar reference numerals are used to designate similar components of an illustrated embodiment.

FIG. 1B shows an exploded view of an example split linac.

FIG. 1C shows the split linac of FIG. 1B where the two split linac portions have been attached to one another.

DETAILED DESCRIPTION

Figure 1A:
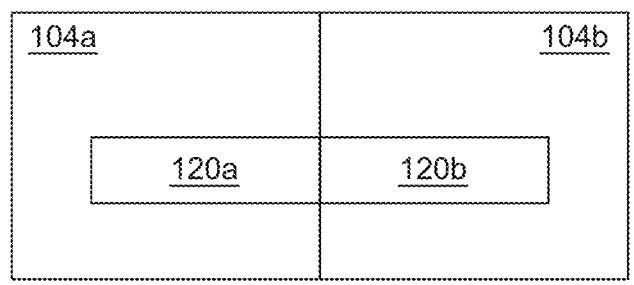
FIG. 1A shows a schematic of an example split linac.

In order to facilitate an understanding of the systems and methods discussed herein, a number of terms are described below. The terms described below, as well as other terms used herein, should be construed to include the provided descriptions, the ordinary and customary meaning of the terms, and/or any other implied meaning for the respective terms. Thus, the descriptions below do not limit the meaning of these terms, but only provide exemplary definitions.

Linear accelerator ("linac"): a device for accelerating particles such as subatomic particles and/or ions where particles pass through each cell only once. A linac is one example of a particle accelerator.

Cell element (or sometimes "cell"): a component of a particle accelerator (e.g., a linear accelerator) that may include a cavity and an iris.

Accelerating cell: a type of cell through which particles are accelerated.

Particles: subatomic or atomic elements, such as electrons or hadrons, that can be accelerated in a particle accelerator.

Phase velocity: rate at which the phase of an electromagnetic wave propagates. The velocity may be positive or negative.

Beam velocity: average rate at which particles within a beam of particles are traveling over a small distance.

Overview of Example Embodiments

Particle accelerators, such as linear accelerators, can be used in a variety of applications, such as medical equipment, X-ray detection systems, radiation detection systems, irradiation, material discrimination, cargo inspection, nuclear forensics, and scientific research, among many other applications. Other accelerators may be cyclic rather than linear. Linear and cyclic accelerators are generally constructed using a plurality of individually manufactured (e.g., milled) cell elements that are then attached to each other using some sort of bonding technique, such as welding. Due to the individual nature of each cell and the subsequent assembly required, frequently these accelerators require tuning and testing after final assembly to fit performance specifications.

Cancer is a global problem, accounting for almost 13% of all deaths worldwide and is one of the fastest growing diseases on earth. Radiation therapy by external beams, as primary treatment or in conjunction with chemotherapy, surgery or other modalities, is used to treat over 60% of cancer patients and used in nearly half of the curative cases. In developed countries, radiation therapy is widely used. However, in low-income and middle-income countries (LMIC), there is a large underserved population, with technology per capita 2 or more orders of magnitude lower than in the US market. LMIC are home to 85% of the world's population, yet they have only around 4,400 radiotherapy systems, an estimated shortage of approximately 5,000 systems. Many LMIC still utilize outdated Cobalt-60 teletherapy machines, which result in excessive normal tissue dose, present safety hazards, and are at risk for diversion for terrorist purposes in radiological dispersal devices (aka "dirty bombs").

The barriers to wider adoption and availability of modern linear accelerator technology in LMIC are primarily due to the high capital and operating costs, requirement for highly-trained service technicians, and high-level of sophistication needed for treatment planning and delivery. In addition, state-of-the-art medical linacs have very high peak and average electrical draws, and require stable, reliable power that is often unavailable in LMIC.

A novel medical linac system can be designed from the ground up to be easy-to-use, simple-in-operation, robust, reliable and efficient.

Radiation therapy is a staple modality in cancer management. By exploiting the differential radiosensitivity between the cancer and normal tissues, radiotherapy can be used to cure cancers including head and neck, breast, prostate and early stage lung cancer and prolong the life of many other types of cancer patients.

The worldwide standard for cancer care is 1 radiation therapy machine for every 100,000 people. In Africa, 29 countries have no machines, Senegal has 1 machine for 12 million people, Ghana and South Africa have 1 machine for 1 million people each, and Ethiopia has 1 machine for 70 million people. The lack of access to radiotherapy contributes to 4 million premature cancer deaths annually.

Both Cobolt-60 and linacs are used to deliver external beam therapy. With the exception of highly specialized machines such as GammaKnife, Co-60 units have been phased out of the developed world, but their replacement by linacs in LMIC has been slow.

There are many technical reasons preventing medical linacs from being more widely available, particularly in the developing world. Such technical reasons include, for example, unstable electrical power, environmental control, and need for filtered, low-conductivity water for cooling.

Certain Example Linac Designs

The design of a linac RF accelerating structure can be improved with particular attention to minimizing the power consumption and reducing fabrication costs. In certain embodiments, the accelerator may advantageously be used in X-band (around 9.3 GHz), instead of the more commonly used S-band (3 GHz). Operation at higher frequency has several advantages compared to lower frequencies, as the effective shunt impedance (which defines power transfer efficiency to the beam) scales as $f^{1/2}$ and dissipated power per unit length as $1/f^{1/2}$. The lower Q of X-band structures also allows the filling time of the cavity to be shorter, reducing the amount of time during which power goes unused. Thus, normal-conducting cavities operating at high frequencies require significantly less power than those operating at low frequencies.

A novel "split-linac" manufacturing approach can be used. Instead of machining dozens of precise individual cells, which may then need to be brazed together and tuned, the RF structure can consist, for example, of just two blocks of copper with a pattern machined into the surface, in which case the two halves can be then joined together through an oven brazing (or other) process. This allows greater precision to be achieved at lower cost by reducing part count and machinist touch time.

In one example, a linac may be engineered using a CAD model with dimensions obtained through iterative RF and design for manufacturing (DFM) modifications to arrive at the final RF volume. Consideration may be given to realistic cutting tool geometries and challenging access to the undercut features of the nose cones.

A preliminary analysis indicates the cost of the conventional side coupled linac machining (e.g., 19 cells, each composed of two half cells) versus the split linac version (e.g., where the RF structure consists of only two parts). Due to the significantly reduced number of parts, and the resulting reduction in machinist setup time, the machining cost of the split structure was dramatically lower, even by a factor of 15. The split design also reduces costs for other manufacturing steps, such as dimensional inspection, cleaning, brazing and tuning. The cost for the split-linac beam centerline may be 70% cheaper compared to alternatives.

Example RF and Beam Dynamics Design

In one embodiment, X-band RF structures can be manufactured as a 6 MeV linac structure. The linac may comprise, for example, a set of bunching cells and a set of accelerating cells, such as, for example, 3 bunching and 16 accelerating side-coupled cells, operating in standing wave regime, as shown below. Example parameters of such a linac are summarized in the table below.

TABLE 1

Calculated parameters of an example X-band medical linac

| | |
|---|---|
| Peak RF power | 1.8 MW |
| Measured shunt impedance | 130 MΩ/m |
| Cavity coupling | 1.65 |
| Peak beam energy | 6.02 MeV |
| Peak beam current | 110.9 mA |
| Duty factor | 0.0008 |
| Pulse flat top | 75% |
| Average beam current | 66.5 µA |
| Dose @ 1 m | 725 cGy/min |
| Dose @ 0.8 m | 1130 cGy/min |

A number of example magnetrons could be used that are listed in Table 2. Of these example magnetrons, L-3 6170 has the highest available peak power, while CPI VMX3100HP has the highest average power.

TABLE 2

Example X-band magnetrons

| Magnetron model | MM7637 | VMX3100HP | 6170 |
|---|---|---|---|
| Manufacturer | NJR | CPI | L-3 |
| Operating Frequency, MHz | 9300 | 9300 | 9300 |
| Peak RF input power, MW | 1.6 | 1.5 | 1.8 |
| Available RF power, MW | 1.5 | 1.4 | 1.7 |
| Duty Cycle | 0.00088 | 0.0018 | 0.0008 |
| Pulse Length, µs | 4.0 | 5.5 | 4.0 |
| Flat Top (Estimated), µs | 3.5 | 5.0 | 3.5 |
| Required peak current, mA (750 cGy/min at 1 m for 6 MeV) | 90 | 45 | 100 |

In some embodiment, the shunt impedance can be increased by reducing the beam aperture size. In this case, the electric field becomes stronger on the axis and the beam acquires more energy with the same RF losses. On the other hand, the beam acceptance may be reduced dramatically and the beam transmission may drop. Also, such structure may have much worse vacuum conductivity and thus cause serious operational problems. The interaction between various linac parameters and the aperture size is summarized in Table 3. Two example cases were considered: optimizing the linac length for the available peak power and maintaining the length for the reference linac (19 cells). The results suggest that a reduced or even minimal length may be achieved with CPI magnetron while a reduced or optimized power consumption may be achieved with L-3 magnetron. For further optimization, we will only consider this magnetron.

TABLE 3

Linac parameters as a function on beam aperture for some example magnetrons

| Aperture, mm | 0.8 | 1.4 | 2.0 |
|---|---|---|---|
| Q-factor | 9385 | 9117 | 8826 |
| Shunt impedance, MOhm/m | 183.4 | 166.7 | 148.7 |
| Structure length (NJR), cm | 21.2 | 23.4 | 26.2 |
| Required power for 19 cells, kW | 1.17 | 1.23 | 1.32 |
| Structure length (CPI), cm | 17.8 | 19.5 | 22.0 |
| Required power for 19 cells, kW | 1.82 | 1.94 | 2.12 |
| Structure length (L-3), cm | 18.7 | 20.5 | 23.1 |
| Required power for 19 cells, kW | 1.10 | 1.15 | 1.23 |

Several types of accelerating structures are disclosed herein, some of which are listed below.

a) Side-coupled structure (SCL). The structures (a-e) operate standing wave (SW) architectures, which may be more efficient than travelling wave (TW) structures for short low-current linacs, since all input RF power may be used;

b) Biperiodic on-axis couple structure (BAS). This structure can have smaller transverse dimensions since the coupling cells may be located between the accelerating cells. Larger dimensions of the coupling holes compared to SCL may allow for better mode stability and/or simpler tuning mechanism. In some configurations, the BAS structure may have lower efficiency compared to the SCL architectures due to one or more coupling cells having zero field located along the accelerating path;

c) Split pi-mode disk-loaded structure (s-DLS SW). Split pi-mode and/or disk-loaded structures can be made from two halves and thus may be much easier and cheaper to machine. Also, such structures may not require time-consuming and expensive post-brazing tuning process since their dimensions may be easily adjusted during the pre-brazing cold tests. The simplest DLS structure that can be fabricated, though, has no noses (poor electric field concentration and no RF beam focusing), and operates in pi-mode, which for 19 cells has miniscule mode separation;

d) A split pi-mode structure with small machinable noses (s-DLSn SW), which improves the on-axis field concentration, and thus shunt impedance;

e) Split SCL (s-SCL) structure that has all the advantages of split structure and the high efficiency of the SCL structure;

f) Travelling wave DLS (DLS TW). TW structures are typically used for high current or high energy linacs, since they don't have a mode separation issue thanks to the continuous dispersion curve, and can be made very long. Also, longer structures have higher full shunt impedance (Rsh*L), which can result is lower power requirement (since, P~V²/Rsh*L). Unlike SW structures, where the filling time may depend on the Q-factor, in TW structure it can depend on the length and group velocity (vgr*L), and may be smaller than in SW. On the other hand, the minimum aperture size can be defined by the minimal group velocity and may be larger than for SW structure, which reduces the shunt impedance;

g) Split TW DLS (s-DLS TW) can provide fabrication simplicity; and h) Backward TW (BTW) structure can avoid or reduce the problem of the minimal aperture, since the coupling between cells can be accomplished by means of magnetic field via coupling holes, unlike DLS where the cells may be coupled by electric fields through the aperture. In BTW the field travels from the end of the structure towards the beginning.

The parameters of above-mentioned structures are compared in Table 4. Certain conclusions of these optimizations include:

Average power losses are mostly defined by the magnetron and the L-3 6170 provides optimal length and power savings;

The average power can be traded off with the structure length. In SW structures, a good way to increase shunt impedance and reduce the required power (by only ~10%) is to make the aperture smaller;

Open pi-mode SW structures with small apertures have lower shunt impedance compared to traditional structures;

Open SCL is possible for the open SW structure. This type of structure can be a good option due to machining advantages;

Constant impedance TW DLS can have comparable parameters to SW linac but may require solenoid in some configurations;

Backward wave constant gradient structures can potentially improve either power losses or the length by 10% comparing to SW structure but cannot be made split.

TABLE 4

Example linac parameters of different types of accelerating structures.

| Structure | Shunt impedance, MΩ/m | Filling time, ns | Structure length (L-3), cm | Required power (19 cells), kW |
|---|---|---|---|---|
| SCL | 148.7 | 453 | 23.1 | 1.23 |
| BAS | 125.5 | 378 | 27.4 | 1.36 |
| s-DLS SW | 124.3 SW | 564 | 27.6 | 1.37 |
| s-DLSn SW | 138.8 | 539 | 24.8 | 1.28 |
| s-SCL | 125.5 | 498 | 27.4 | 1.36 |
| DLS TW | 168.5 | 357 | 22.8 | 1.27 |
| s-DLS TW | 136.6 | 222 | 28.0 | 1.37 |
| BTW | 186.8 | 177 | 21.5 | 1.13 |

Based in these simulations, a split side-coupled structure (s-SCL) may be used because it can have comparable parameters to the traditional structure and may be easier for fabrication, assembly and tuning (discussed below).

During the RF design phase, consideration was given to realistic cutting tool geometries and challenging access to the undercut features of the nose cones. The cutting tool depth to diameter ratio may be kept below 2 to promote tool rigidity useable for high surface finishes and surface feature dimensional conformance. Several design modifications may be made compared to the direct SCL structure adaptation presented in the figure below in order to allow feasible fabrication, as shown below:

The cylindrical shape of the coupling cell may be changed to the rectangular;

The corner blending radius may be increased;

Sharp coupling hole edge may be replaced with the oval conjunction.

Similarly, the bunching cells with the reduced phase velocity ($\beta_{ph}=v/c$) may be designed with cell parameters summarized in Table 5.

TABLE 5

| s-SCL cell parameters | | |
|---|---|---|
| Phase β | 0.65 | 0.999 |
| Cell length, cm | 1.048 | 1.61 |
| Shunt impedance, MΩ/m | 89.4 | 124.3 |
| Coupling between cells, % | 3.3 | 2.5 |
| Mode separation, MHz | ~8 | ~6 |
| Q-factor | 6692 | 9224 |

Based on these parameters, the preliminary beam dynamics analysis was performed in Parmela to demonstrate the feasibility of such linac approach (mostly, in terms of beam focusing). The concept of the accelerator was similar to the conventional X-band linac produced by RadiaBeam (three bunching and 16 accelerating cells). However, here all bunching cells were made similar (with β=0.65) to simplify fabrication. This became possible since the linac is planned to operate in a single energy regime. An example field profile in the bunching cells is shown below. The same figure demonstrates an example simulated beam energy spectrum at the end of the linac. The simulated linac parameters are presented in Table 6, and demonstrate features of the s-SCL structure.

TABLE 6

| Simulated s-SCL linac parameters | |
|---|---|
| Energy | 5.96 MeV |
| Peak current | 118 mA |
| Gun current | 283 mA |
| Transmission | 42% |
| E-field gradient | 28 MV/m |

Cooling features may be included therein, such as 5 mm diameter water channels in each element (e.g., half) with a typical heat transfer coefficient for the cooling water of 15 kW/m$^2$/K. RF losses may be considered equally distributed (e.g., 567 W per half). Example preliminary simulation results for various number of channels are shown below and reasonable cooling may be achieved with 6 channels per half.

Engineering and Fabrication of Certain Embodiments

To significantly reduce the linac costs, a novel "split-linac" manufacturing approach may be used. Instead of machining dozens of precise individual cells, which are generally then be attached (e.g., brazed) together and tuned, the RF structure comprises (e.g., consists of) a plurality of (e.g., two) blocks of metal (e.g., copper) with a pattern machined into the surface. The blocks (e.g., two halves) are then joined together through an oven brazing process. This allows greater precision to be achieved at lower cost by reducing part count and machinist touch time as detailed further herein.

The design and size of configurations described herein can allow multiple parts to be manufactured simultaneously on a single machine setup that can reduce the average touch time per block (e.g., half).

The split structure fabrication process can also eliminate and/or reduce the time-consuming step of tuning the blocks. Currently, the deviations from the designed dimensions in the final assembly are the result of machining feature deviations and variances in braze material thicknesses in between the cells. The machining accuracy can be high enough to significantly reduce tuning time. Certain surface profiles within the structures may be kept to +/−15 microns along with corresponding profile positions, and in some configurations within +/−10 microns. This level of accuracy can result in high quality RF performance.

Advantageously, a split linear or cyclic accelerator can be manufactured. The split accelerator can include two sections that are subsequently joined. Each section can include a portion (e.g., half) of a one or more cells such that once the sections are joined together, the one or more cells are complete. In contrast with the accelerators described above where individual, complete cell components are manufactured and then assembled to create the accelerator, a split accelerator architecture allows for the construction or manufacture of fewer elements or portions, such as two halves. Each portion can be tuned during the manufacturing process so that little or no tuning is required after the final assembly. Because in some embodiments the spacing, sizing, proportions, and other dimensions of subsequent cell portions is at least partially already determined (e.g., since the cell portions are milled from a common block of metal), tuning requirements may be reduced or eliminated after manufacture of each accelerator portion. The reduction in the number of individual components that need to be manufactured and/or tuned can result in savings of time and cost in manufacturing and/or tuning.

Various embodiments disclosed herein employ a novel "split-linac" manufacturing approach that is highly compatible with micromachining. The term "split linac" may be used throughout, but the functionality may be applied to cyclic accelerators as well. Instead of machining dozens of precise individual cells, which often must then me brazed together and tuned, the accelerating structure may comprise two blocks of metal (e.g., copper) with a pattern micromachined into the surface. The two blocks may then be joined together (e.g., welded, brazed, or diffusion bonded). This allows greater precision to be achieved at lower cost, reduces part count, eliminates issues with braze materials changing the dimensions of the cavities, and potentially eliminates the need for tuning.

Below are several additional examples of linac structures and manufacturing processes. Any of the details noted above, e.g., related to developments and/or optimizations identified through various experiments, may be applicable in various combinations in the examples provided below.

Split Structure Particle Accelerators

A compact accelerating structure can comprise two milled halves, capable of producing an energetic (e.g., between about 0.1 MeV to 10 MeV) electron beam and converting the beam to X-ray radiation. The accelerating structure may have compact dimensions that can utilize an X- and/or K-band (including Ku- and Ka-sub-bands) magnetron. An S- and/or C-band wave generator can also be used. A lower-cost structure is achieved by reducing the number of elements to two pieces (comprising, for example, copper) with micro-milled accelerating cells.

The structures relate to linear accelerators and more particularly to compact split-structure accelerators that operate at microwave frequencies to drive an accelerating wave through the structure, which comprises two manufactured (e.g., micro-machined, electrical discharge machined (EDM)) portions of a diaphragmed waveguide to enable low-cost production. The structures may also be used in cyclic accelerators, such as circular accelerators. For example, the split accelerator may be applied to microtrons.

Such compact accelerating structures can be used in a variety of contexts, such as X-ray production or electron production. X-ray sources are used in a wide range of applications from cancer therapy to oil exploration. Some of the applications of these sources include non-intrusive inspection and active interrogation systems, such as methods for nuclear detection, material recognition, and industrial radiography. The structures may also be used in medical applications, material or cargo inspection (e.g., using X-ray backscatter) or other computed tomography applications.

A cheap and compact X-ray source can utilize radioactive materials to produce X-rays. Replacement of radioisotopes used in these applications with a safer, electronic alternative enhances the above-mentioned methods with new capabilities, and reduces the risk of radioisotopes being used in radiological dispersal devices.

Particle accelerators can be used as X-ray sources by utilizing a Bremsstrahlung effect of X-ray radiation production by the deceleration of an electron by an atomic nucleus. However, conventional accelerators cannot compete with radioisotope sources in terms of compactness and cost. X-ray tubes can be used as a compact source of X-rays, but for the energies of 0.1-1 MeV that radioisotopes are mostly used they are still very bulky and expensive.

It is known that the volume of the accelerating structure scales inversely with the square of the operation frequency f (e.g., it may scale approximately with $1/f^{5/2}$), and by building an accelerator that operates at frequencies higher than the conventional linacs do (>3 GHz), it is possible to reduce the dimensions of the X-rays source to a portable size where it can compete with radioisotope sources. However, operation at such high frequencies has several limiting factors: availability of power sources, high dimensional sensitivity and extreme complexity of tuning and operational accelerating wave stability, and high price of accelerating waveguide fabrication with conventional separate cell technology.

The split linac design can provide a method of achieving a reduced cost of ultra-high gradient structures for high-energy physics accelerators as well. Split linacs can be micro-machined or molded. To machine the linac, an electrical discharge machining (EDM) process or other machining process may be used to achieve a dimensional tolerance of less than about 100 μm and may be less. For example, the techniques described herein may achieve a surface roughness of less than 5 μm and in some embodiments about 1 μm. Additionally or alternatively, a surface roughness of less than 1 μm may be achieved, such as about 200 nm.

Split linac designs described herein may be used at higher frequencies to both reduce the size of the linac and to reduce the manufacturing costs. Electromagnetic wave sources, such as magnetrons, can be used to provide K-band (e.g., Ku-band and/or Ka-band), X-band, and/or C-band frequencies. The split linac approach changes the paradigm of manufacturing and opens up the possibility of using modern micromachining approaches to achieve the required tolerances at very low cost.

Various embodiments can include a Ku-band (e.g., around 16 GHz) RF power magnetron. Ku-band RF can allow reduction in the size of X-band accelerator by about 44%. Ku-band magnetrons are relatively small and inexpensive and may require lower-voltages from the modulator. The Ku-band magnetron can produce up to 250 kW or more. In some cases, and without being limited by theory, a 60 kW peak power may be enough to provide 1 MeV energy to the electron beam in 20 cm length. A 1 kW peak power may be required for every 1 mA of accelerated current.

Some examples of uses of accelerators is in various detection systems, such as detectors for radioactive materials. Approximately 5,000 devices containing 55,000 high-activity radionuclide sources are in use in the United States today, in applications ranging from cancer therapy to oil exploration. Measurement of radioactive materials can be used as a tool to safeguard nuclear facilities. Enrichment plants can represent one of the most sensitive parts of the nuclear fuel cycle, yet safeguards at enrichment plants still remain a challenge for the International Atomic Energy Agency (IAEA). IAEA and the United States Department of Energy (DOE) have identified the replacement of radioactive sources with alternative technologies as a priority due to the risk of accidents and diversion by terrorists for use in Radiological Dispersal Devices.

Turning now to the figures, various embodiments and variations of those embodiments will now be disclosed. FIG. 1A shows a schematic of an example split linac 104. The split linac 104 may include a first split linac portion 104a and a second split linac portion 104b. Each split linac portion 104a, 104b may include corresponding accelerating structure portions 120a, 120b. The accelerating structure portions 120a, 120b may include various features as described herein. For example, each of the accelerating structure portions 120a, 120b may include corresponding cell portions or other aspects that may cooperate with one another in providing linac functionality. As shown, the split linac portion 104a may be disposed adjacent the split linac portion 104b. Additionally or alternatively, the accelerating structure portion 120a may be in optical communication with the accelerating structure portion 120b to provide linac functionality as described herein.

FIG. 1B shows an exploded view of an example split linac 104. The split linac 104 can include first and second split linac portions 104a, 104b as shown. One or more of the first and second split linac portions 104a, 104b may include a corresponding first linac entrance aperture portion 112a and/or a corresponding linac entrance aperture portion 112b (not shown in FIG. 1B). Additionally or alternatively, corresponding first and second linac exit aperture portions 116a, 116b may be included in the first and second split linac portions 104a, 104b. When the first and second split linac portions 104a, 104b are joined, the first and second linac entrance aperture portions 112a, 112b can form a linac entrance aperture 112. Additionally or alternatively, the linac exit aperture portions 116a, 116b can form a linac exit aperture 116. The linac entrance aperture 112 and/or the linac exit aperture 116 can define a beam axis 108. The split linac 104 can be configured to receive a beam of particles (e.g., protons, electrons, etc.) along the beam axis 108. The split linac 104 can be configured to receive the beam of particles into the linac entrance aperture 112 and to allow the beam to exit via the beam axis 108. As shown, an accelerating structure portion 120a may be included within the split linac portion 104a.

Each split linac portion 104a, 104b may include corresponding first and second RF input coupling element portions 124a, 124b and/or first and second RF output coupling element portions 128a, 128b. The combination of the first and second RF input coupling element portion 124a, 124b can form an RF input coupling element 124. Similarly, the combination of the first and second RF output coupling element portion 128a, 128b can form an RF output coupling element 128. The RF input coupling element 124 and/or the RF output coupling element 128 may be referred to as RF coupling cells.

The RF coupling cells can be configured to incouple/outcouple Ku-band RF power. Other wavelengths (e.g., X-band, S-band, etc.) are possible. Generally, the RF power is fed (e.g., from a power source such as a magnetron) into the split linac 104 via the RF input coupling element 124. In some embodiments, such as those involving side-coupled cells, a single coupling element (e.g., the RF input coupling element 124) is used. In other embodiments, such as certain traveling wave embodiments, the split linac 104 can outcouple excess RF power via the RF output coupling element 128.

FIG. 1C shows the split linac 104 of FIG. 1B where the two split linac portions 104a, 104b have been attached to one another. The split linac portions 104a, 104b may be attached in any number of ways. For example, the two split linac portions 104a, 104b may be welded, brazed, diffusion bonded, or adhered using another technique. The attachment between the split linac portion 104a and the split linac portion 104b may be along at least a portion of a seam 130. The split linac portion 104a may have an attachment surface and the split linac portion 104b may have a corresponding attachment surface, which are brought adjacent to one another for final attachment. One or both of the split linac portions 104a, 104b may include copper (e.g., pure copper, a copper alloy copper or other metal (e.g., stainless steel, aluminum, niobium, etc.). The complete split linac 104 may have a substantially regular shape. For example, the split linac 104 may be substantially a rectangular prism, as shown in FIG. 1C.

The split linac 104 can be used in a variety of applications that may necessitate different lengths and/or other dimensions. For example, the length of the split linac 104 (as measured along the beam axis) may be between 5 cm and 150 cm, between about 10 cm and 80 cm, and in some embodiments is about 30 cm. Longer linac structures may require higher RF power. The split linac 104 may operate at an energy of between about 4 MeV and 9 MeV and in some embodiments operates at an energy of about 6 MEV.

The split linac 104 may operate using a standing wave (SW) setup. However, in some embodiments, a traveling wave (TW) configuration may be used. The split linac 104 can operate on a variety of frequencies. The split linac 104 may be configured to operate in either $\pi/2$-mode or $\pi$-, but other configurations may be possible in TW regime (e.g., about $2\pi/3$-mode). The split linac 104 may be configured to receive an energy of less than about 10 MeV. The frequency of the RF power may be greater than about 6 GHz, greater than about 9 GHz, and in some embodiments may be greater than about 15 GHz. In some embodiments, the operation frequency may be between about 3 GHz and 300 GHz, and between about 9 GHz and 110 GHz in some embodiments. The energy may be received from an energy source described herein.

While various examples of a "split linac" are discussed herein with two split linac portions (e.g., 104a, 104b), in other embodiments a split linac may include additional portions. For example, a split linac may include three, four, or more split linac portions configured to be joined to form a linac. For example, in one embodiment, four quarter-portion linacs, each comprising substantially half of one of the split linacs 104a or 104b, can be joined to form a linac.

Figure 2:
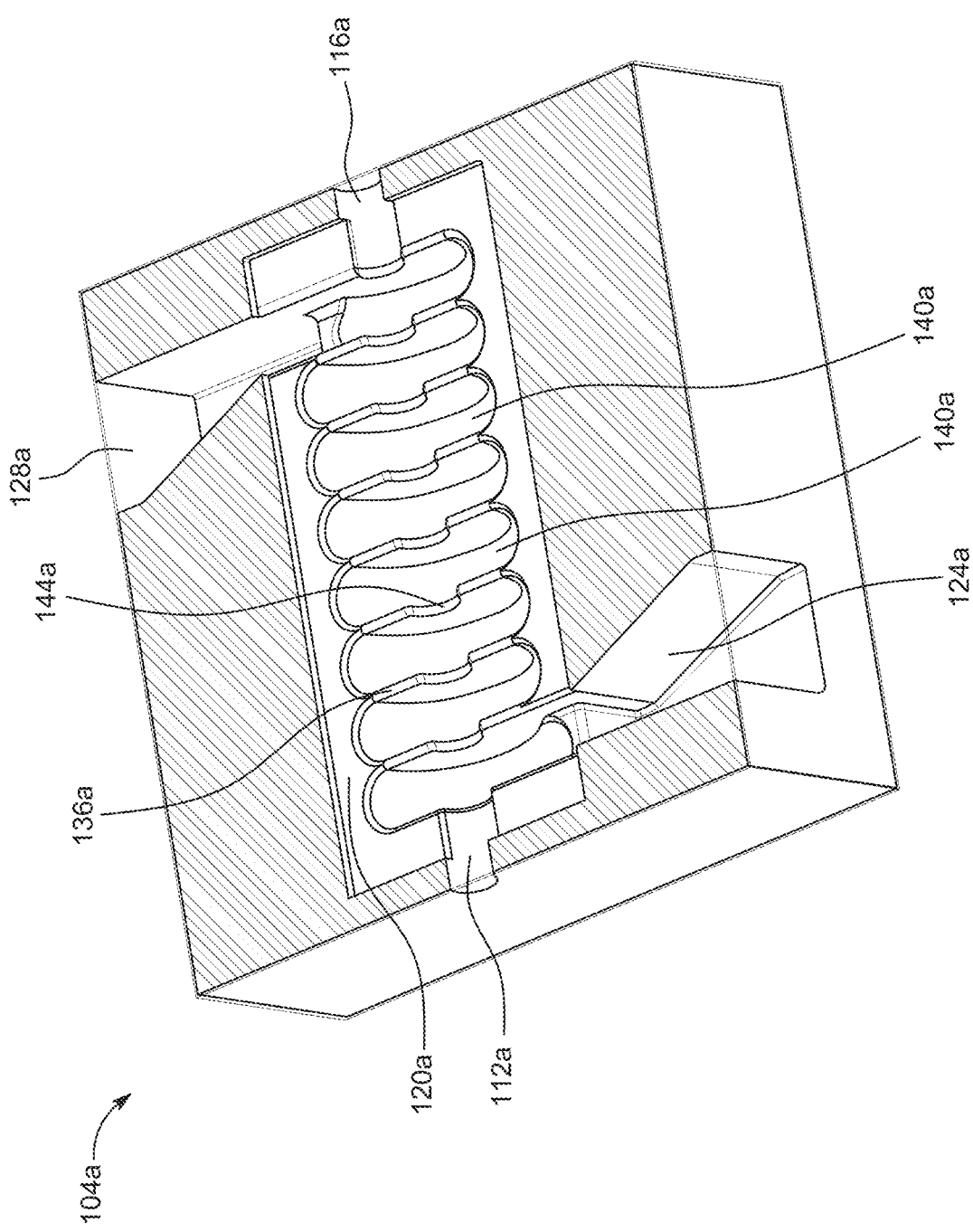
FIG. 2 shows a detail view of an example split linac portion shown in FIG. 1B.

FIG. 2 shows a detail view of an example split linac portion 104a shown in FIG. 1B. The split linac portion 104a can include the linac entrance aperture portion 112a, the linac exit aperture portion 116a, the RF input coupling element portion 124a, and the RF output coupling element portion 128a as described herein. The accelerating structure portion 120a may include a recessed portion from an attachment surface (indicated by the hashed area). The accelerating structure portion 120a can include one or more accelerating cell portions 140a. Between or within each accelerating cell portion 140a, a cell iris portion 136 may be disposed. The cell iris portion 136 may include a raised portion relative to neighboring one or more accelerating cell portions 140a. The a split linac portion 104a having a substantially semi-cylindrical internal surface with a plurality of ridges. Each of the plurality of ridges can be spaced apart along the beam axis 108 of the split linac portion 104a. Each of the plurality of ridges can extend radially from the semi-cylindrical internal surface. The attachment surface (e.g., bonding surface) may be included outside a region of the accelerating structure portion 120a. The second split linac portion 104b may have one or more features of the split linac portion 104a such that the split linac portion 104a and the split linac portion 104b may be attached to one another. In some embodiments, the split linac portion 104a and the split linac portion 104b exhibit partial or complete point symmetry (e.g., about a center point of the accelerating structure portion 120a and/or the accelerating structure portion 120b).

Each of the accelerating cell portions 140a can include a hollow space having the shape of a semi-cylinder or disk shape. The shape may be elliptical (e.g., ellipsoid, ovoid) or some other rounded shape. The portions removed to form the accelerating structure portions 120a can be removed radially from the beam axis 108. A length of each accelerating cell portion 140a may be measured between neighboring cell iris portions 136a. In some cases, the length of each accelerating cell portion 140a may be measured such that a given cell iris portion 136a is disposed at a center of the length.

Each of the cell iris portions 136s can include a corresponding plurality of iris aperture portions 144a therein. Each of the iris aperture portions 144a can be formed (e.g., milled, molded) to form a semi-circular space in the corresponding cell iris portion 136a when viewed along the beam axis 108. Accordingly, the portion removed for each iris aperture portion 144a can be in the shape of a disk or semi-cylinder. Each cell iris portion 136a can include a smooth surface.

The RF coupling element portions 124a, 128a can each have a narrowest portion nearest the accelerating structure portion 120a (e.g., radially proximal of the accelerating structure portion 120a) and an expanded portion or flared portion radially distal of the accelerating structure portion 120a.

The formation of the resulting split linac 104 can include taking a split linac portion 104a and a corresponding split linac portion 104b such that a spacing between respective pairs of adjacent ridges of the plurality of ridges of the split linac portion 104a along the beam axis 108 is approximately equal to a spacing between corresponding pairs of adjacent ridges of the plurality of ridges of the split linac portion 104b along the beam axis. The attachment surface of the split linac portion 104a and the corresponding attachment surface of the split linac portion 104b can be attached (e.g., bonded) together to define a joined structure. The structure can have a substantially cylindrical internal surface with corresponding ridges that form a plurality of accelerating cells 140. Each of the accelerating cell 140 can have a central aperture that is configured to allow a beam of charged particles to travel therethrough along the beam axis 108 extending through iris aperture 144 of each of the plurality of accelerating cells. Each of the split linac portion 104a and the split linac portion 104b can have corresponding RF input coupling element portion 124a and RF input coupling element portion 124b that form a resulting RF input coupling element 124 when finalized. Similarly, a RF output coupling element portion 128a and a RF output coupling element portion 128b can form a resulting RF output coupling element 128. The plurality of accelerating cells 140 can be in optical and/or fluid communication with the RF input coupling element 124 and/or the RF output coupling element 128. The RF input coupling element 124 can receive electromagnetic waves from a power source (e.g., a magnetron). The RF input coupling element 124 may be in communication with a first accelerating cell 140 and/or the RF output coupling element 128 may be in communication with a last accelerating cell 140. Each of the plurality of accelerating cells 140 may be configured to accelerate a beam of charged particles to a velocity of 0.1, 0.2, 0.3, 0.4, 0.5, 0.6, 0.7, 0.8, 0.9, or less than 1.0 times the speed of light, any value therebetween or within any range therein. The accelerating structure portion 120a can include one or more pluralities of accelerating cells 140. Each of the pluralities of accelerating cells 140 can be configured for accelerating particles at a different velocity or range of velocities relative to neighboring a neighboring plurality of accelerating cells 140. For example, subsequent pluralities of cells can be configured for accelerating the beam of particles at increasingly higher velocities. For more details, see, for example, FIG. 3.

Figure 3:
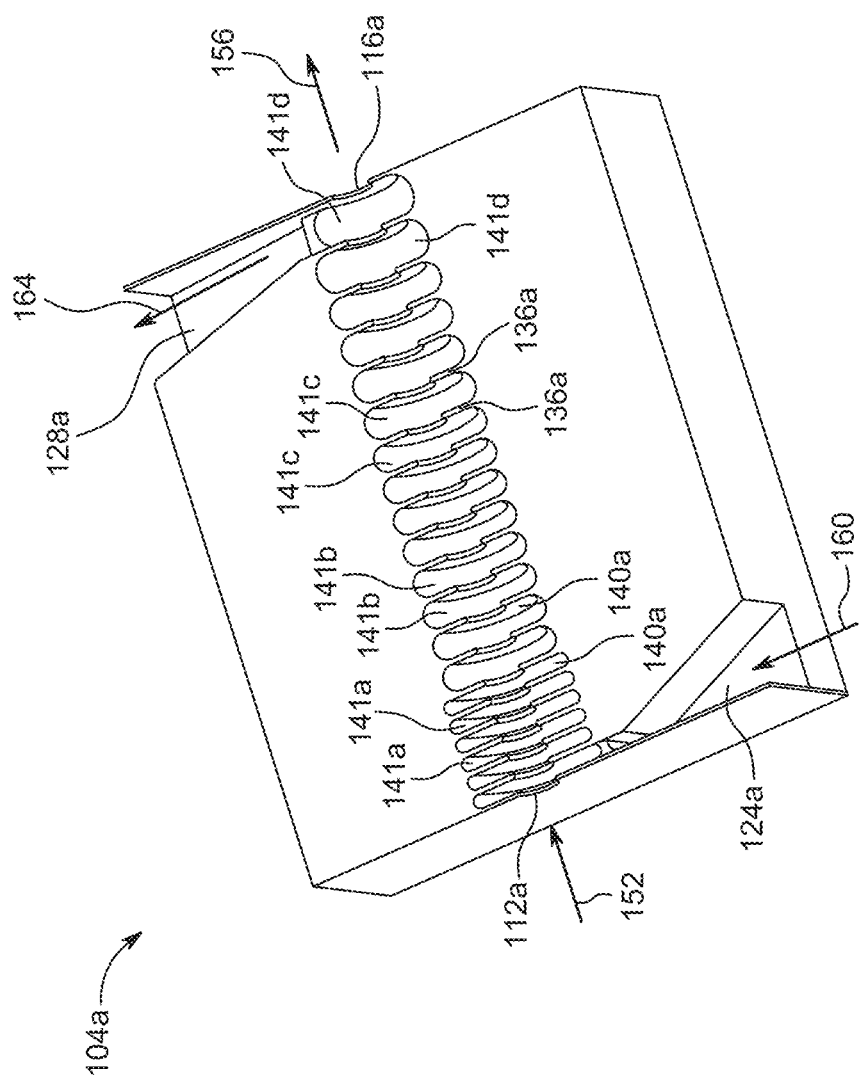
FIG. 3 shows another example of a split linac portion.

FIG. 3 shows another example of a split linac portion 104a. The split linac portion 104a shown in FIG. 3 does not include an accelerating structure portion 120a, but such an accelerating structure portion 120a can be included. As shown, a beam input 152 can represent an input for a beam of particles. A corresponding beam output 156 can represent an output of the beam of particles. The beam input 152 and the beam output 156 can be aligned with corresponding linac entrance aperture portions 112a, 112b and/or with corresponding linac exit aperture portion 116a, 116b. An RF input 160 can be via the RF input coupling element 124 and/or an RF output 164 can be via the RF output coupling element 128.

The plurality of accelerating cell portions 140a can include one or more cell types 141a, 141b, 141c, 141d. The first cell type 141a can be configured to accelerate particles at a velocity (which may roughly correspond to a phase velocity of the RF waves) of between about $\beta=0.2$ and $\beta=0.9$, between about $\beta=0.3$ and $\beta=0.8$, and in some embodiments at about $\beta=0.6$. The second cell type 141b can be configured to accelerate particles at a velocity of between about $\beta=0.2$ and $\beta=1.0$, between about $\beta=0.3$ and $\beta=0.9$, and in some embodiments at about $\beta=0.65$. The third cell type 141c can be configured to accelerate particles at a velocity of between about $\beta=0.3$ and $\beta=1.0$, between about $\beta=0.5$ and $\beta=0.95$, and in some embodiments at about $\beta=0.7$. Additional or fewer cell types may be included. In some embodiments, cells of the various types may be arranged in different quantities and/or orders than illustrated. In some embodiments, subsequent cell types are configured to accelerate particles at increasingly higher velocities. For example, in some embodiments, each cell of the first cell type 141a is configured to accelerate cells at about $\beta=0.6$, each cell of the second cell type 141b is configured to accelerate cells at about $\beta=0.65$, each cell of the third cell type 141c is configured to accelerate cells at about $\beta=0.7$. Other configurations are also possible, such as cells with generally increasing $\beta$ that have one or more higher-$\beta$ initial cells (e.g., $\beta_1=0.65$, $\beta_{2-n}>0.45$, where the subscript refers to the cell number, with n being the total number of cells in the accelerator). The symbol beta ("$\beta$") can represent a ratio of the speed of light. For example, $\beta=0.4$ indicates a speed of 0.4 times the speed of light.

Figure 4:
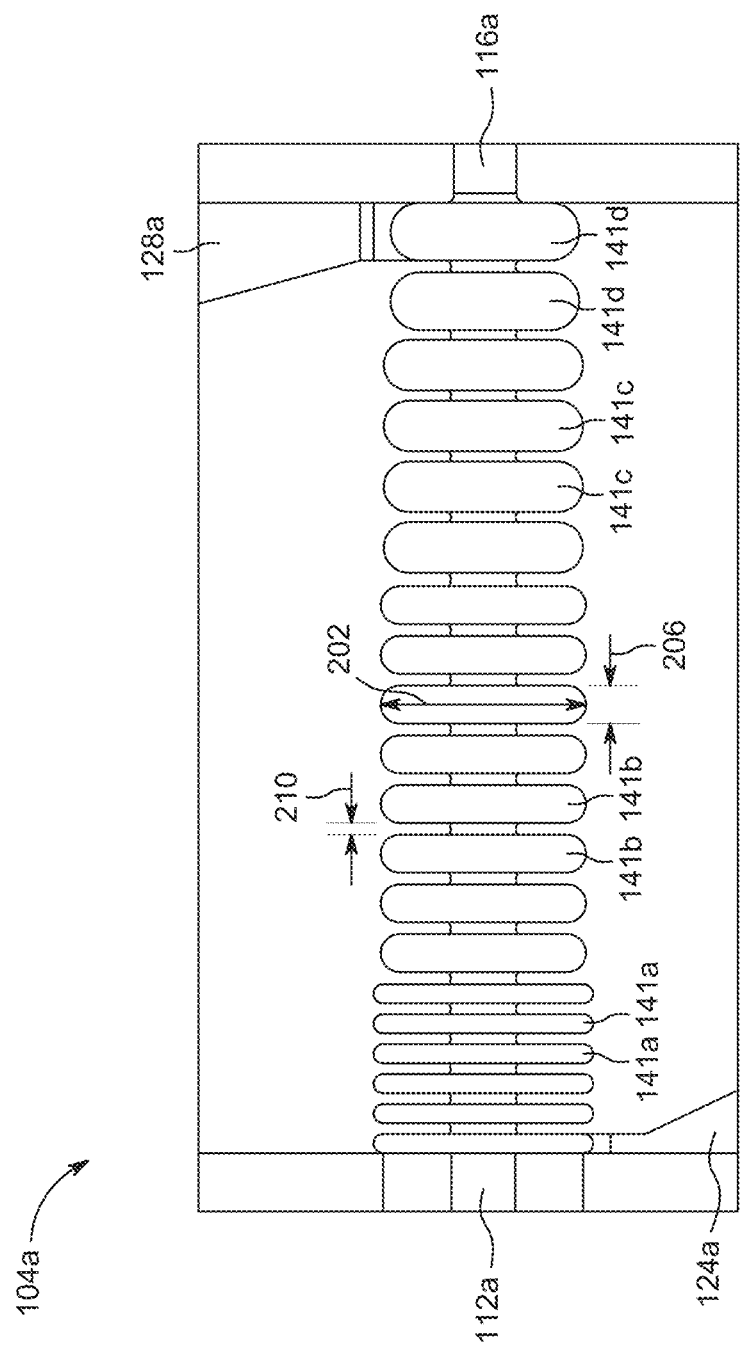
FIG. 4 shows a top view of another example of a split linac portion.

FIG. 4 shows a top view of another example of a split linac portion 104a. Throughout this description, while detail has been provided for a split linac portion 104a, a corresponding split linac portion 104b may similarly be constructed to form a resulting split linac 104. As shown in FIG. 4, each cell type 141a, 141b, 141c, 141d can have different physical parameters, such as those shown (though the cells may not be drawn to scale). An aspect ratio can be defined as a ratio of the cell diameter 202 to the cell length 206. The aspect ratio for cells may be 0.1, 0.2, 0.3, 0.4, 0.5, 0.6, 0.7, 0.8, 0.9, 1, 1.2, 1.4, 1.6, 1.8, 2, 2.5, 3, 3.5, 4, 4.5, 5, 6, 7, 8, 9, 10, 11, 12, 13, 14, 15, 16, 17, 18, 19, 20, any value therein, or fall within any range within any value therein. For example, in some embodiments, the aspect ratio may be about 1, 1.5, 8, or about 11, though other values are possible. The aspect ratio may decrease for subsequent cell types 141a, 141b, 141c, 141d along the beam axis 108.

The number of accelerating cells 140 of each cell type 141a, 141b, 141c, 141d may vary for each cell type. For example, the split linac 104 may include a greater number of lower-beta cells (e.g., accelerating cells 140 configured to accelerate particles at a relatively lower velocity than other accelerating cells 140) than higher-beta cells. The first cell type 141a can include between one and twenty cells, between two and fifteen cells, and in some embodiments (e.g., as shown) includes six cells. The second cell type 141b can include between one and thirty cells, between two and twenty cells, and in some embodiments (e.g., as shown) includes eight cells. In some embodiments the second cell type 141b can include between five and fifteen cells The third cell type 141c can include between one and fifteen cells, between two and twelve cells, and in some embodiments (e.g., as shown) includes four cells. The fourth cell type 141d can include between one and twelve cells, between two and ten cells, and in some embodiments (e.g., as shown) includes two cells. Additional or fewer cells 140 within each cell type may be included. The number of total cell types can be equal to or less than the total number of cells 140. For example, in some embodiments, each cell in the split linac 104 is unique and/or constitutes its own cell type. In some embodiments, the number of cell types is equal to one (e.g., all the cells are identical). Any number of cell types therebetween are possible. The split linac 104 can include between 1 and 120 accelerating cells 140, between 5 and 60 cells, and in some embodiments includes, for example, about 6, 8, 20, or 35 cells. In some embodiments, an initial accelerating cell 140 has a lower beta than a final accelerating cell 140. The beta value of groups of cells or individual cells may generally increase along the optical axis. For example, each cell may be configured to accelerate particles at a higher velocity (e.g., the cells have a higher beta) than each preceding cell. Other configurations are possible, such as others disclosed herein.

Figure 5:
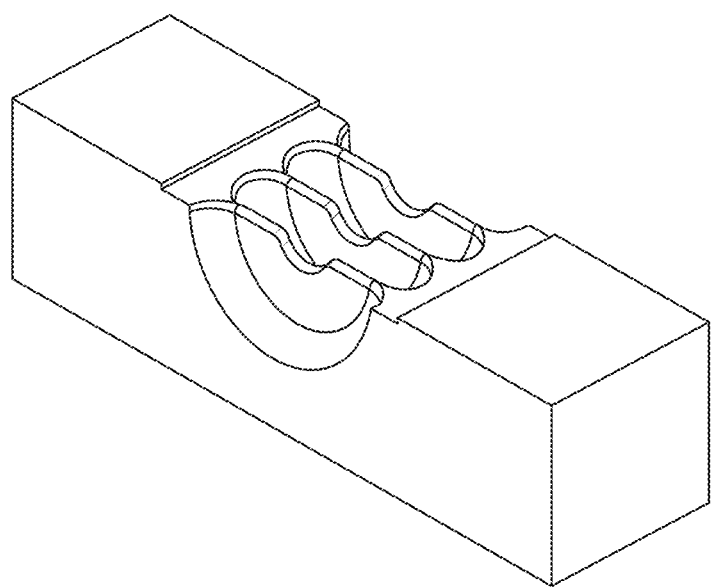
FIG. 5 shows an isometric view of a section of a split linac portion, including a section of an accelerating structure portion.
Figure 6:
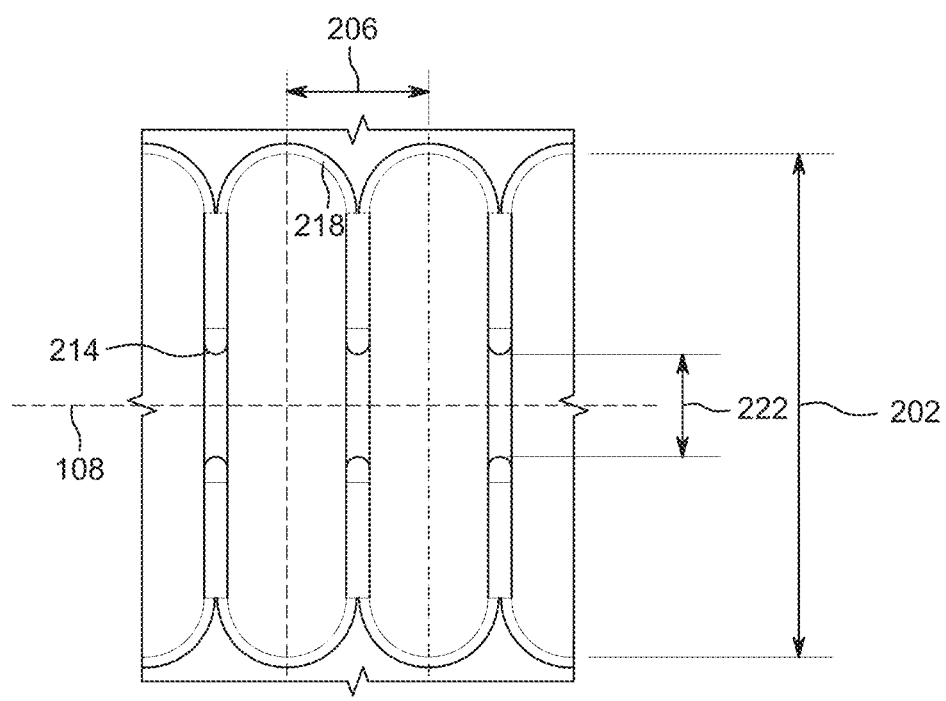
FIG. 6 shows a top view of an example section of a split linac portion.

FIG. 5 shows an isometric view of a section of a split linac portion 104a, including a section of an accelerating structure portion 120a. FIG. 6 shows a top view of an example section of a split linac portion 104a. Various dimensions are indicated. For example, a cell length 206 is shown as measured along the beam axis 108 such that the cell iris 136 is disposed at a midpoint along the cell length 206. The cell length 206 may be determined in part by the velocity of the beam of particles (which may be symbolized as "beta" ($\beta$)) and/or the wavelength of the EM waves ($\lambda$). The velocity of the beam of particles may be approximately equal to the phase velocity of the waves. The cell length 206 may be determined by a product of $\beta$ and $\lambda$. For example, the cell length 206 (L) may be given by $L=\beta*\lambda*\theta/2\pi$, where $\theta$ is the phase advance of the cell 140. In certain wavelengths, the cell length 206 may scale with $\beta$ such that the cell length 206 is approximated by $\beta$ multiplied by 6.1 mm. The cell length 206 may be between about 0.5 mm and 5.5 cm, between about 1 mm and 6 mm, and in some embodiments is about 2 mm or 3 mm (depending on the cell type). For example, using S-band waves operating at a $\pi$-mode with $\beta=1$, the cells may be as long as about 5.5 cm. For a similar architecture in C-band, the cells may be about 2.6 cm. Shorter cells may be used, for example, when using Ka-band at a $\pi/2$-mode. Such cells may be about 0.9 mm long. Other variants are possible depending on the desired implementation.

The cell diameter 202, as measured perpendicular to the beam axis 108, can vary based on the type of cell, the wavelength used, and the velocity of the beam of particles. The cell diameter 202 can be between about 1 mm and 10 cm, between about 3 mm and 2 cm, and in some embodiments is about 1 cm, 8 cm, or 9 cm (depending on the cell type). The iris thickness 210 can be between about 0.1 mm and 30 mm, between about 0.3 mm and 2 mm, and in some embodiments is about 0.7 mm (depending on the cell type). The cell diameter 202 can be associated with the frequency of the RF power. For example, the chosen RF power may determine in part what the cell diameter 202 is. The iris thickness 210 may be advantageously small, but this may be limited by structural and thermal features of the split linac 104.

Other dimensions are shown, such as an iris blend radius 214 and a cell blend radius 218. The iris blend radius 214 can depend in part on the iris thickness 210. The iris blend radius 214 can be between about 0.05 mm and 5 mm, between about 0.1 mm and 1 mm, and in some embodiments is about 0.4 mm (depending on the cell type). The cell blend radius 218 can depend on the cell length 206 and/or on the iris thickness 210. It may be advantageous to improve the cell blend radius 218 by increasing the Q-factor. The maximum cell blend radius 218 may be determined by half the difference between the cell length 206 and the iris thickness 210. The cell blend radius 218 can be between about 0.05 cm and 20 cm, between about 1 cm and 5 cm, and in some embodiments is between about 0.3 cm and 0.5 cm or is about 2.5 cm (depending on the cell type). The cell blend radius 218 may advantageously be as large as possible to allow for improved linac operation. The iris aperture diameter 222 can be between about 0.1 mm and 50 mm, between about 1 mm and 15 mm, and in some embodiments is about 8 mm. The iris aperture diameter 222 can be associated with (e.g., be determined by) the strength of the field produced in the split linac 104.

Figure 7:
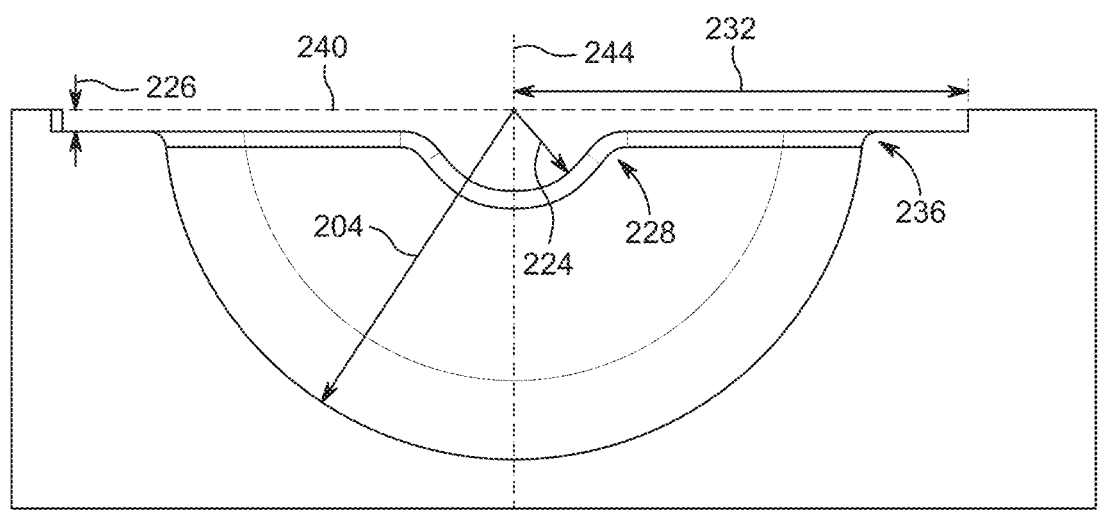
FIG. 7 shows additional dimensions of an example split linac portion.

FIG. 7 shows additional dimensions of an example split linac portion 104a that may be considered. A cell radius 204 is shown, which is half of the cell diameter 202. An iris aperture radius 224 is shown. The iris aperture radius 224 can be defined by an intersection of a gap plane 240 and a bisecting plane 244. The gap plane 240 may be coplanar, for example, with an attachment surface of the split linac portion 104a. A distance between the gap plane 240 and an accelerating surface can be given by a gap half-width 226, as shown. A transition between the accelerating surface and the surface defining the cell radius 204 can be described as a gap blend radius 236. A transition between the accelerating surface and a surface defining the iris aperture radius 224 can be described as an iris blend radius 228. A distance between the bisecting plane 244 and an end of the accelerating surface can be described as a gap half-length 232. The bisecting plane 244 can divide the split linac portion 104a into two portions where each accelerating cell portion 140a is bisected by the bisecting plane 244.

The split linac 104 can have various dimensions that may take on various values. For example, the cell radius 204 may be between about 1 mm and 100 mm, between about 5 mm and 65 mm, and in some embodiments is about 10 mm (e.g., at Ka-band) or about 90 mm (e.g., at S-band). The iris aperture radius 224 may be between about 0.5 mm and 20 mm, between about 2 mm and 15 mm, and in some embodiments is about 10 mm. The gap half-width 226 may be between about 0.5 mm and 15 mm, between about 1 mm and 10 mm, and in some embodiments is about 3 mm. The gap half-length 232 may be between about 0.5 cm and 10 cm, between about 2 cm and 7 cm, and in some embodiments is about 5 cm. In some embodiments, the gap half-length 232 is greater than the cell diameter 202. The iris blend radius 228 may be between about 0.5 mm and 35 mm, between about 1 mm and 20 mm, and in some embodiments is about 10 mm. The gap blend radius 236 may be between about 0.5 mm and 35 mm, between about 1 mm and 20 mm, and in some embodiments is about 10 mm.

Figure 8:
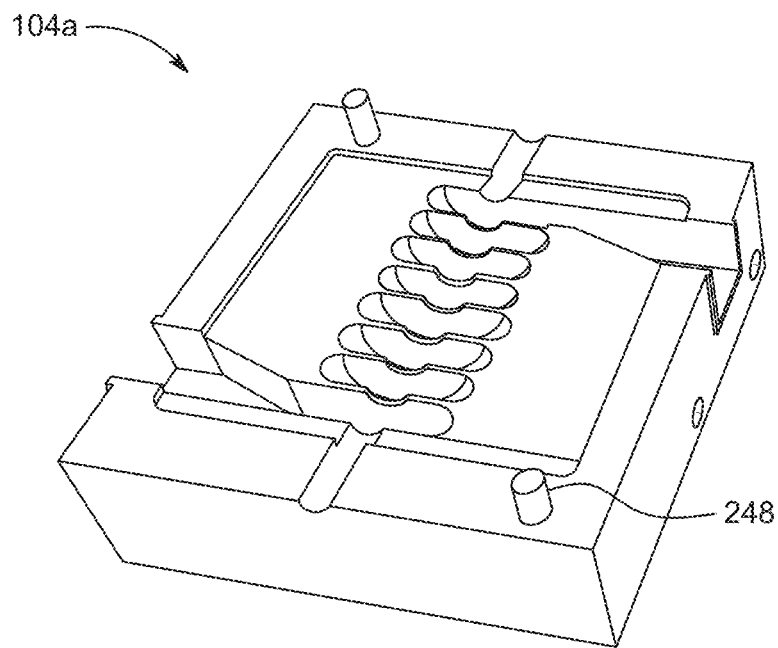
FIG. 8 shows an example split linac portion.
Figure 9:
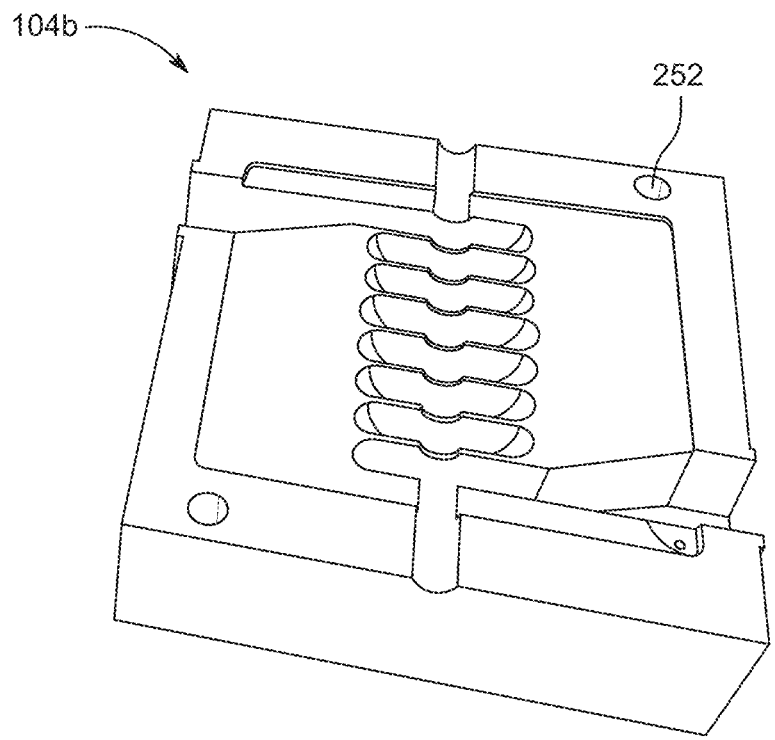
FIG. 9 shows an example split linac portion that can be attached to the split linac of FIG. 8.

FIGS. 8 and 9 show an example split linac portion 104a and an example split linac portion 104b, respectively. As shown, the split linac portion 104a can include one or more connecting elements 248. The split linac portion 104b can include corresponding one or more receiving portions 252. Each receiving portion 252 can receive a corresponding connecting element 248. The connecting element 248 may be a rod, a joint, a protrusion, or any other type of connector. The receiving portion 252 may be an opening, a recess, an attachment device, or any other type of device configured to receive the connecting element 248. In some embodiments, the connecting element 248 and receiving portion 252 are sufficient to keep the split linac portions 104a, 104b together and/or aligned sufficiently to undergo a bonding (e.g., welding, brazing, etc.) process.

Figure 10:
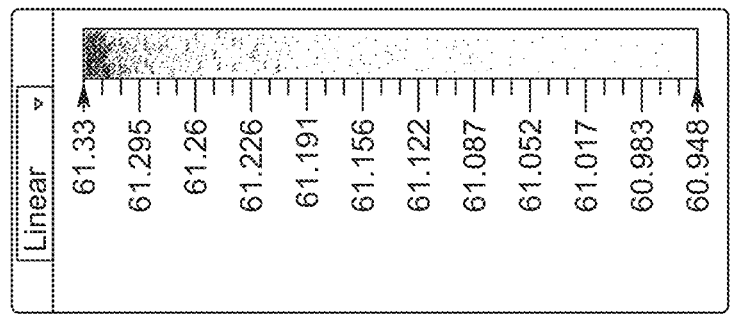
FIG. 10 shows a thermal performance heat map of an example split linac.
Figure 10:
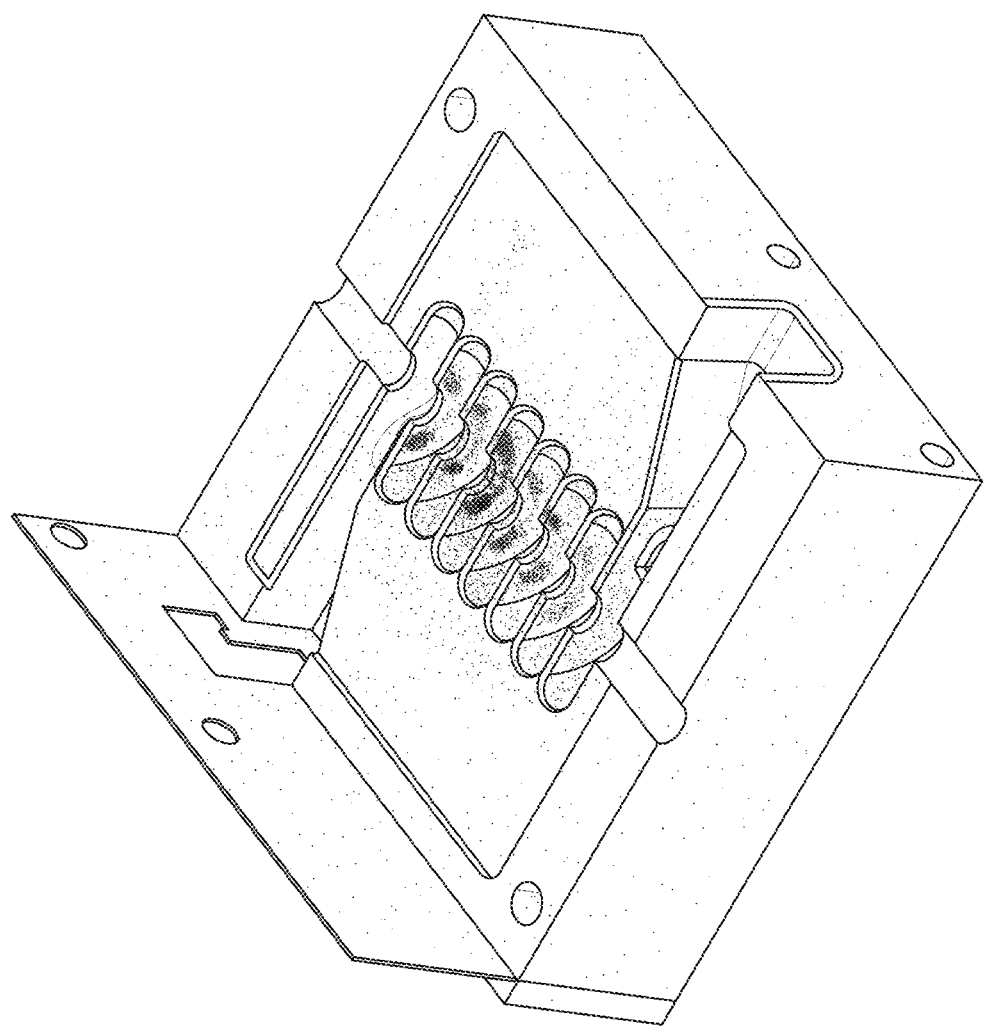

FIG. 10 shows a thermal performance heat map of an example split linac 104. The heat load shown assumes 50 W of RF average power. Two boundary conditions were considered: natural air convection (heat transfer coefficient of about 10 W/m$^2$K) and forced air convection from a moderate airflow fan with heat transfer coefficient of about 25 W/m$^2$K, which corresponds to less than about 5 m/s air flow speed. As shown in FIG. 17, the temperature of the structure rises from 20° C. to 40° C., but the temperature gradient inside the structure remains below 0.5° C. The temperature gradient (e.g., difference between two temperatures in the split linac 104) can indicate potential thermal deformations inside the structure and/or frequency deviations of the structure. Thus, lower temperature gradients can be advantageous.

Figure 11:
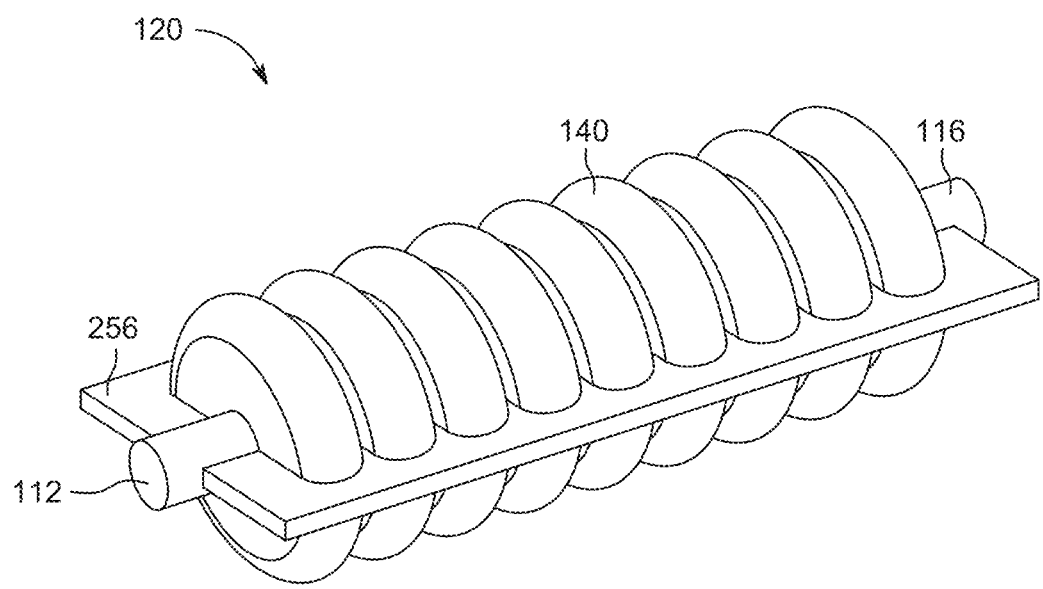
FIG. 11 shows an example accelerating structure.

FIG. 11 shows an example accelerating structure 120. The accelerating structure 120 may represent the negative space that is occupied by air/vacuum in one or more embodiments of the split linac 104 described herein. The accelerating structure 120 can include a plurality of accelerating cells 140 in sequence. However, as noted above, the accelerating cells 140 may be in a cyclic structure, such as a circular accelerator (e.g., microtron). As shown, the accelerating structure 120 can include a gap 256, which is indicated with reference to various embodiments of a split linac 104 herein. The accelerating structure 120 can include a linac entrance aperture 112 and a linac exit aperture 116. While the accelerating structure 120 is shown as having 9 cells, other configurations (including more or fewer cells) are possible. The gap 256 can advantageously allow for better vacuum pumping and/or for preventing beam break up (e.g., current instability). The gap 256 may also reduce the strain on the material of the split linac 104, such as copper or other material described herein. Reduced strain can allow for operation at greater temperatures, thus allowing for higher energy use and/or allowing for reduced cooling necessity.

Figure 12A:
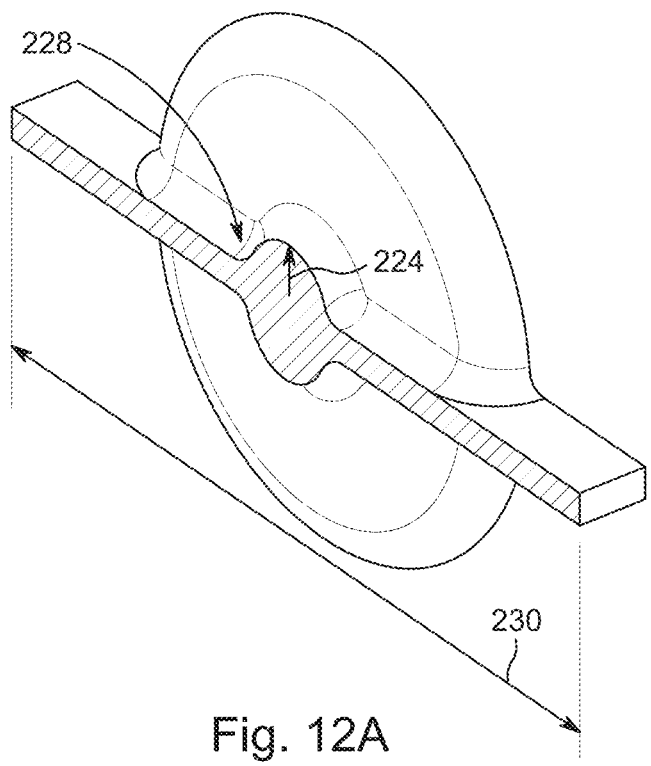
FIG. 12A shows an isometric view of a portion of an accelerating cell.
Figure 12B:
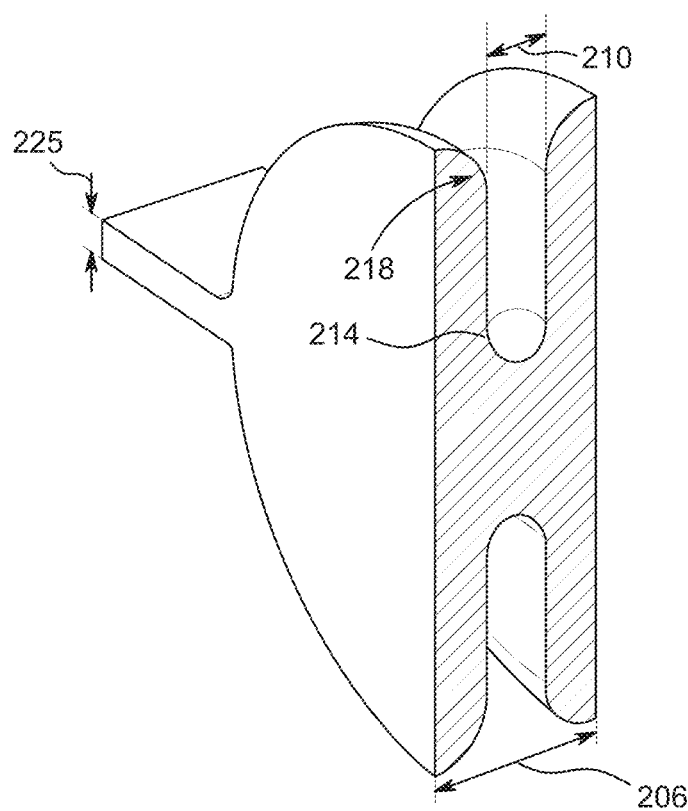
FIG. 12B shows some additional dimensions of an example accelerating cell.

FIGS. 12A-12B show portions of the accelerating structure 120 shown in FIG. 11. FIG. 12A shows an isometric view of a portion of an accelerating cell 140 with various dimensions labeled. Some dimensions are disclosed elsewhere herein. The gap length 230 may be between about 5 mm and 200 mm, between about 10 mm and 150 mm, and in some embodiments is about 20 mm. FIG. 12B shows some additional dimensions of an example accelerating structure 120. For example, the gap width 225 may be between about 0.1 mm and 30 mm, between about 1 mm and 10 mm, and in some embodiments is about 6 mm. The gap width 225 may be related to the wavelength of the RF power. For example, the gap width 225 can be greater than about 1 mm, which may depend on the frequency of the RF power. In some embodiments, the cell length 206 may be less than about half the wavelength.

Figure 13:
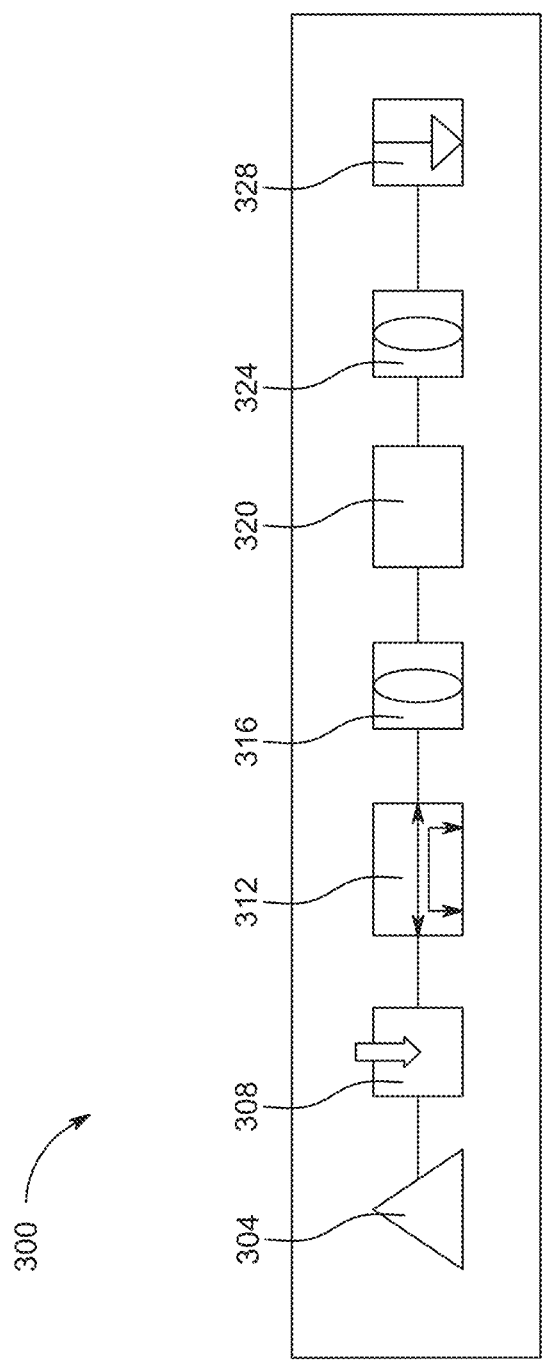
FIG. 13 shows a schematic of an example RF waveguide network.

FIG. 13 shows a schematic of an example RF waveguide network 300. The RF waveguide network 300 can include an energy source 304, a fluid inlet 308, a detector 312, an RF inlet aperture 316, a waveguide 320, a RF outlet aperture 324, and/or a capture device 328. The waveguide 320 can be purged with a fluid or gas (e.g., $SF_6$) to prevent the risk of arcing. The waveguide 320 may correspond to the accelerating structure 120 and/or the split linac 104 described herein. To isolate the vacuum volume of the accelerator from the waveguide, one or more microwave windows may be attached to the waveguide 320. The passive devices may have a ceramic barrier (e.g., ultra-high purity alumina) to block gas while still allowing microwave power to flow. To terminate the unused RF power, there may be a ferrite load at the output of the structure. The RF waveguide network 300 may be a particle source, such as a commercial diode gun with small cathode (e.g., less than 3 mm diameter) and focusing electrodes. The detector 312 may include a reflectometer. The RF waveguide network 300 can include a driver, such as a gun driver. The driver may be configured to provide approximately constant power to heat a filament inside a thermionic cathode. The gun driver may produce the HV pulses (e.g., 15 kV) to cause the gun to emit electrons and provide enough initial acceleration for the linac to efficiently capture the particles. In some embodiments, a thermionic gun may be used, which can emit electrons from a cathode heated to a sufficiently high temperature. The electron gun driver may be integrated with a magnetron modulator. The magnetron modulator's output may be tapped at a lower voltage portion of the circuit, which may allow driving the energy source 304 with the same pulse.

Figure 14A:
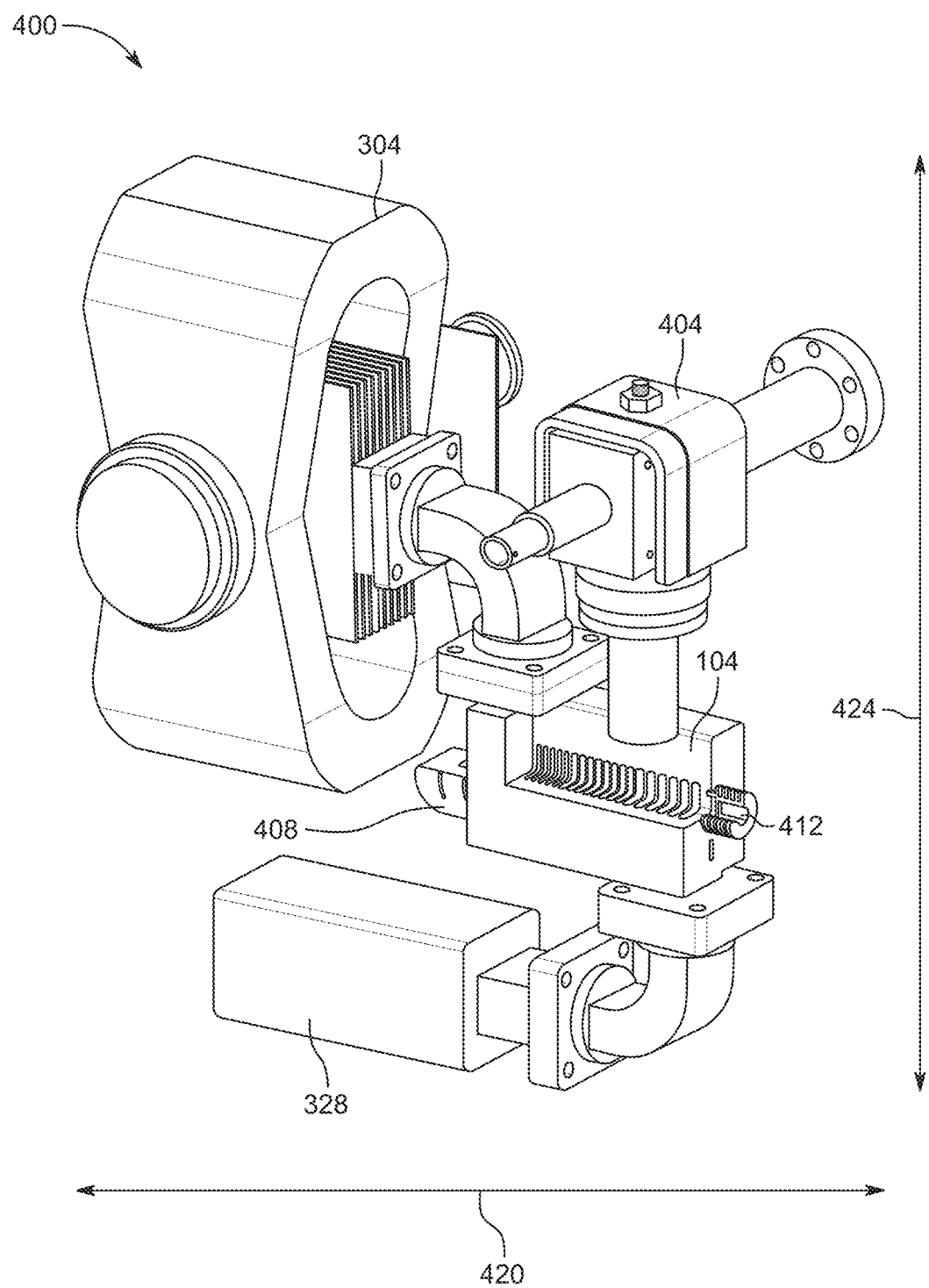
FIG. 14A shows an example linac head.
Figure 14B:
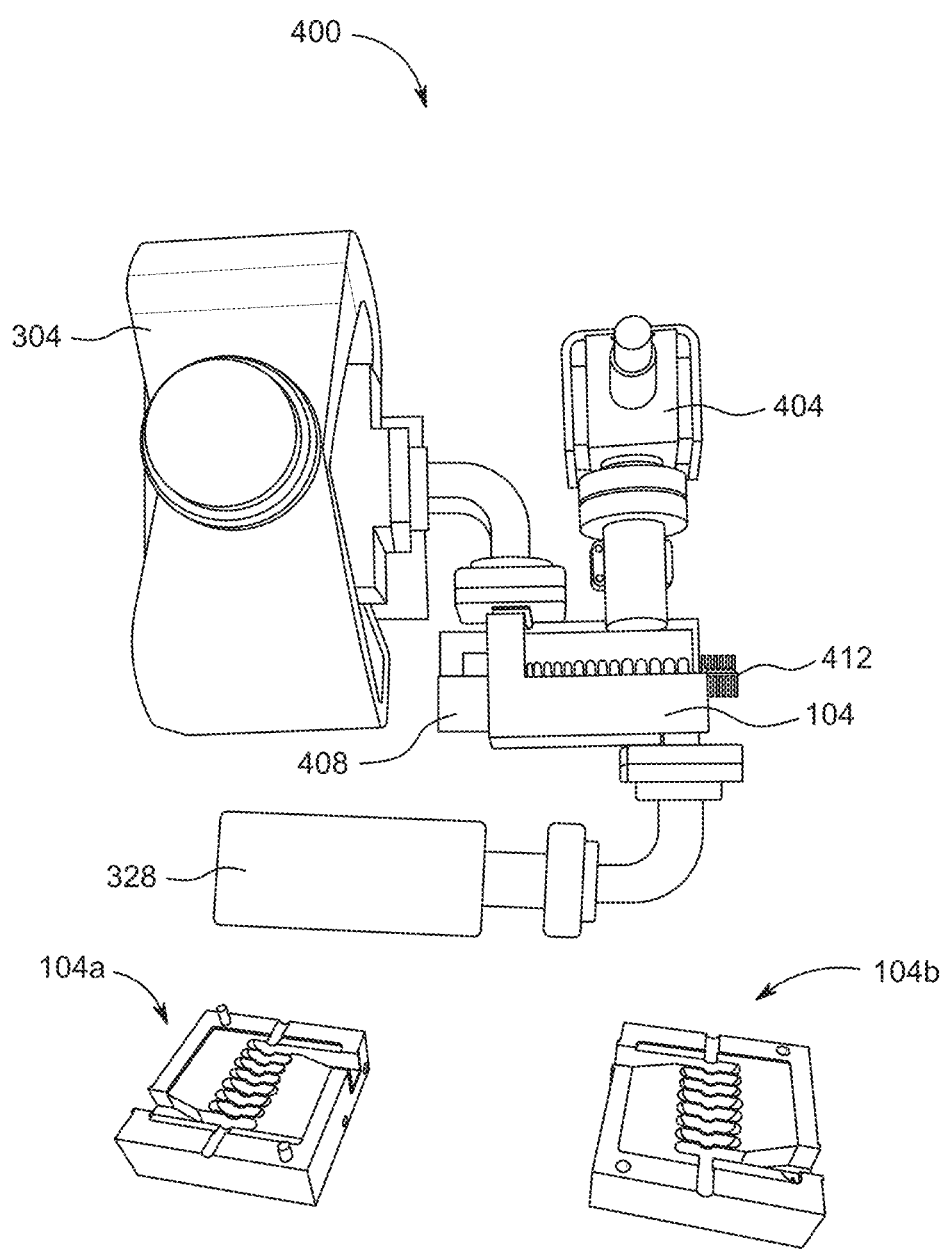
FIG. 14B shows another angle of the linac head, including the split linac portions.

FIG. 14A shows an example linac head 400 that may include one or more components described herein, such as those shown in FIG. 13. FIG. 14B shows another angle of the linac head 400, including the split linac portions 104a, 104b as an approximate size comparison. The individual elements may not necessarily be shown to scale. The linac head 400 may be included in a larger device, such as a detector, an X-ray machine (e.g., for medical applications), irradiation, material discrimination, cargo inspection, nuclear forensics, or some other device. As shown, the linac head 400 can include an energy source 304, a particle source 408, a vacuum pump 404, a split linac 104, a converter 412, and/or a capture device 328. The energy source 304 can be any energy source configured to emit electromagnetic waves for pumping into a split linac 104. For example, a magnetron may be used, such as a Ku-band magnetron. A lighter energy source 304 may be advantageous to allow, for example, for hand-held operation of the linac head 400. Additionally or alternatively, a relatively low anode voltage may be advantageous to reduce the power consumption and/or increase the efficiency of the energy source 304. The particle source 408 can include an electron gun, such as a diode electron gun. The energy source 304 can be configured to emit waves tuned to accelerate particles emitted by the energy source 304. The energy source 304 can inject energy into the split linac 104, such as through an input coupling element (e.g., the RF input coupling element 124 described herein). The energy source 304 can produce between about 10 kW and 250 kW, between about 25 kW and 95 kW, and in some embodiments produces about 50 kW power. In some embodiments, the energy source 304 can produce between about 200 kW and 3 MW. Higher energy sources (e.g., magnetrons up to 7 MW) can be used. The amount of power produced may be larger than a minimum necessary power (e.g., 40 kW). A safety margin between the power output and the minimum required output can allow operation in a lower power mode that may extend the lifetime of the energy source 304.

The particle source 408 can be configured to inject particles into the split linac 104 along a beam axis or optical axis. The output current may be regulated with the cathode temperature. For example, a high current density small dispenser cathode may be used to provide a relatively stable emission of up to 170 mA and/or up to or more than 10,000 hrs operation with greater than 95% of the initial cathode current. The cathode may have a diameter of only 1.45 mm. In other embodiments, an off-the-shelf compact diode electron gun may be used. Such an electron gun may be simpler to incorporate into the design and may have a focusing electrode to improve the acceptance of the beam.

The vacuum pump 404 can be configured to create and/or maintain a vacuum within the accelerating structure (e.g., the accelerating structure 120 herein) of the split linac 104. The total vacuum volume of the linac head 400 is relatively small, especially compared to conventional linacs. Accordingly, pumps with lower rates of pumping can be used. For example, rates such as 10 l/s may be sufficient for this device. Non-evaporable getter (NEG) pumps may be used. Such pumps may employ a hybrid pumping mechanism that uses a renewable chemical absorption pump (the NEG element) and a small ion pump. This may promote larger pumping speeds in a relatively compact package. For example, the pump may have a 100 l/s NEG element combined with a 5 l/s ion pump. After activation, the NEG element may require no electrical power. Thus, in some embodiments, the linac head 400 power requirements and weight can be reduced. When the system is stored, the ion pump can be reconnected to remove the noble gases that the NEG pump cannot.

The split linac 104 can have between 10 and 50 cells, such as those described herein. In some embodiments, the particles (e.g., electrons) can be incident on a converter 412 to produce energy, such as X-rays. The capture device 328 can be configured to receive an RF load capable of dissipating up to about 100 kW of peak RF power, up to about 80 kW, and in some embodiments up to about 60 kW of peak RF power.

The linac head 400 can be configured to fit into specific dimensions. It may be advantageous to create a smaller, more compact linac head 400 that can be hefted by a human. For example, the linac head 400 may have a linac head width 420 and a linac head height 424. The linac head width 420 can be between about 5 cm and 120 cm, between about 8 cm and 90 cm, and in some embodiments is about 18 cm. The linac head height 424 can be between about 10 cm and 200 cm, between about 15 cm and 150 cm, and in some embodiments is about 20 cm. The linac head depth (not shown in FIG. 14A) can be between about 3 cm and 70 cm, between about 5 cm and 50 cm, and in some embodiments is about 10 cm. The linac head 400 can have a total interior volume of between about 100 cm$^3$ and 15000 cm$^3$, between about 300 cm$^3$ and 10000 cm$^3$, and in some embodiments is about 3600 cm$^3$. A total weight of the linac head 400 can be between about 1 kg and 80 kg, between about 3 kg and 25 kg, and in some embodiments is about 5 kg.

Figure 15A:
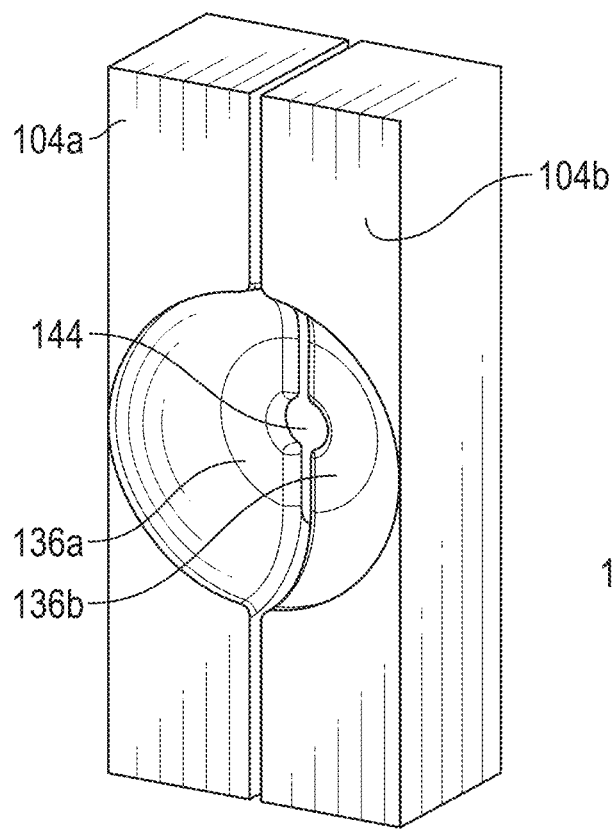
FIG. 15A shows an example portion without a nose in the iris.
Figure 15B:
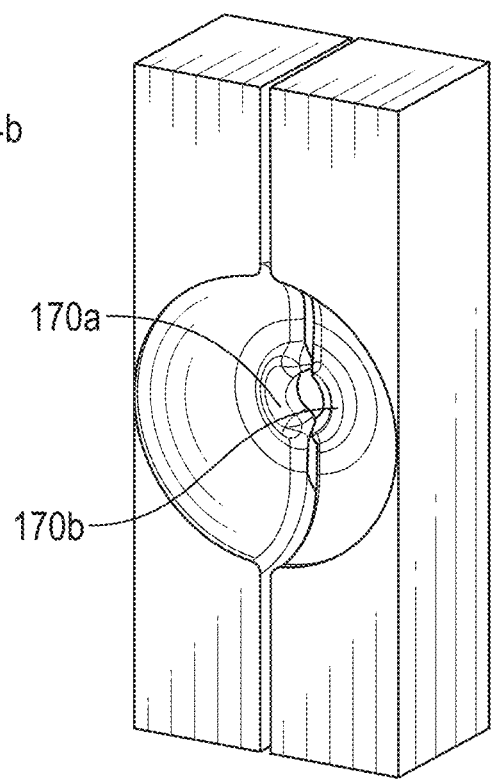
FIG. 15B shows example split linac portions having iris nose portion.

FIGS. 15A-15B show two examples of cross sections of portions of a split linac assembly operating in a standing wave configuration. FIG. 15A shows an example portion without a nose in the iris and FIG. 15B shows split linac portions having iris nose portions 170a, 170b (which together comprise iris nose 170). The iris nose portions 170a, 170b can be configured to increase shunt impedance. As is described in more detail herein, each iris nose 170 (and/or corresponding iris nose portions 170a, 170b) may include increasing thickness in the corresponding cell iris 136 radially along a portion of the cell iris 136, as shown. Just radially from the iris aperture 144 of the corresponding cell iris 136, the iris nose 170 may include a decrease in thickness of the cell iris 136. Accordingly, a cross-section of the iris nose 170 can include opposing nose-shaped structures. Details of various embodiments of such noses are described in more detail herein. Additional details are included in PCT Application No. PCT/US2018/030980, filed May 3, 2018, entitled "COMPACT HIGH GRADIENT ION ACCELERATING STRUCTURE," which is hereby incorporated by reference herein in its entirety and for all purposes.

The iris nose 170 can be described using one or more of a number of dimensions. A slope of the iris nose 170 can be described by a nose rise angle. The nose rise angle can be between about 35° and 90° (e.g., no nose at all) and in some embodiments is between about 50° and 75°. In some embodiments the nose rise angle is about 66°. A maximum thickness of the iris nose 170 can be between about 0.2 mm and 15 mm and in some embodiments is between about 0.4 mm and 11 mm. In some embodiments the maximum thickness of the iris nose 170 is about 1 mm. A ratio of the maximum thickness of the iris nose 170 and the iris thickness is between about 1 (no nose) and 8, and in some embodiments is between about 2 and 5. In some embodiments, the ratio is about 3. The iris nose 170 can include an increased thickness of a portion of the joint structure between neighboring cells of the first plurality of cells such that the increased thickness is relative to one or more regions surrounding the nose of the portion of the joint structure.

As noted, FIGS. 15A-15B may correspond to portions of cells that are used in a π-mode structure (e.g., standing wave (SWG)). Such a structure may be used in an open structure configuration. In open structures, there may be a gap between corresponding elements (e.g., halves) of the linac (e.g., a gap indicated by the gap width 225). Open structures may reduce problems related to the surface mismatch after the elements are attached. The cell diameter 202 (not labeled) may be any value described herein, such as between about 1 cm and 5 cm or about 2.5 cm. The iris aperture diameter 222 (not labeled) may be any value described herein, such as between about 0.5 mm and 5 mm. The shunt impedance may be any value described herein, such as between about 100 MΩ/m and 150 MΩ/m.

Figure 16A:
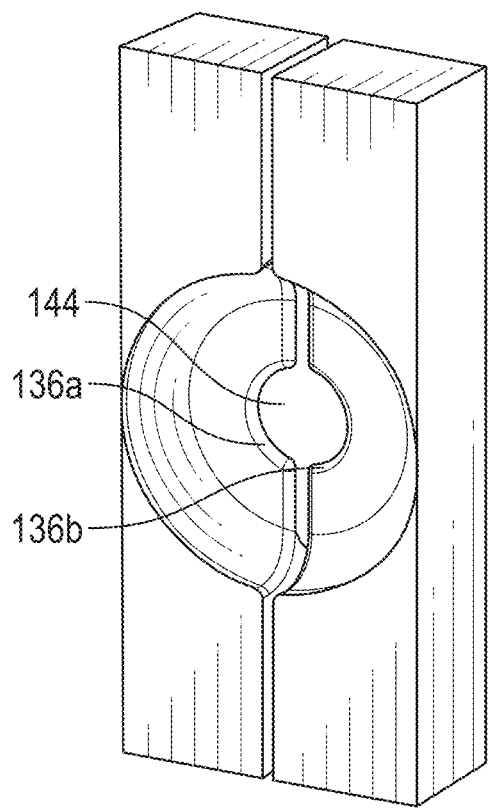
FIG. 16A shows an example of cross sections of portions of a split linac assembly operating in a traveling wave configuration.
Figure 16B:
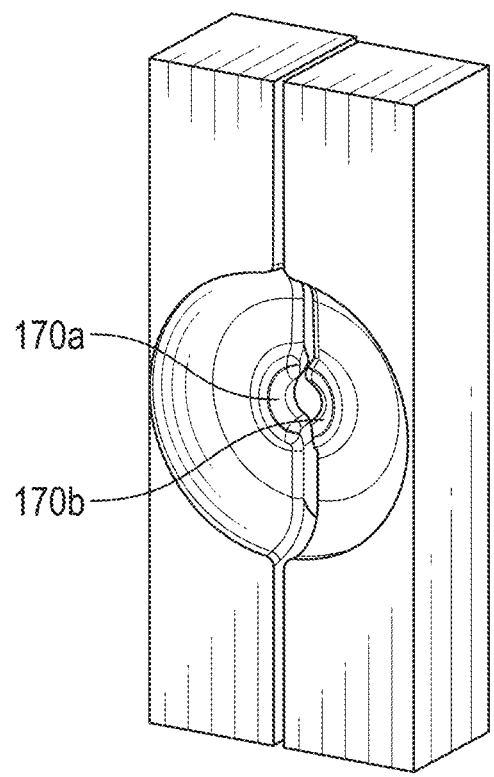
FIG. 16B shows an example of cross sections of portions of a split linac assembly operating in a traveling wave configuration.

FIGS. 16A-16B show two examples of cross sections of portions of a split linac assembly operating in a traveling wave (TW) configuration. As shown the iris aperture 144 may be larger in TW linacs than in SW linacs. Advantageously, a larger iris aperture 144 (e.g., greater iris aperture diameter 222) may reduce filling time of the cells. The iris aperture diameter 222 can allow for a range of filling times, such as between about 250 ns and 1000 ns. In some embodiments, the filling time can be less than 500 ns and in some embodiments is less than 250 ns, less than 200 ns, and in certain embodiments has a filling time of about 160 ns.

Figure 17C:
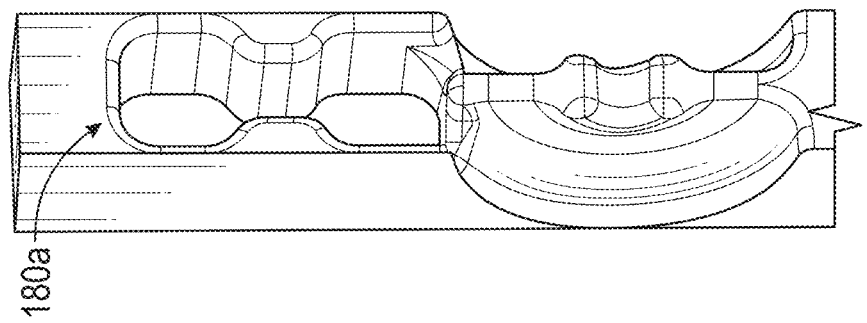
FIG. 17C shows an example side cell portion.
Figure 17B:
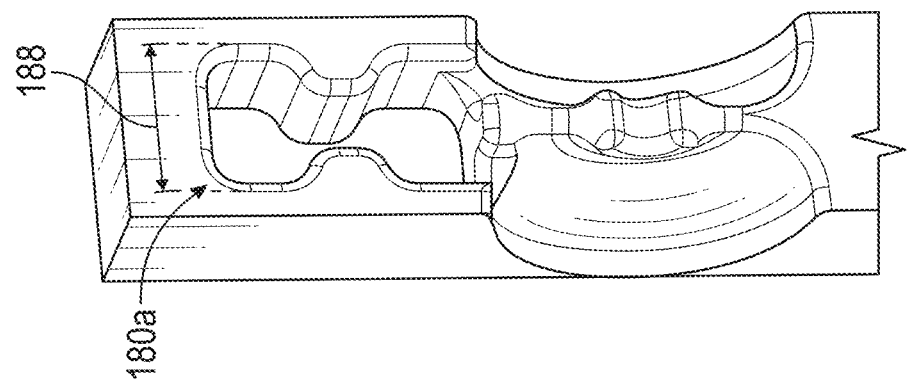
FIG. 17B shows an example side cell portion.
Figure 17A:
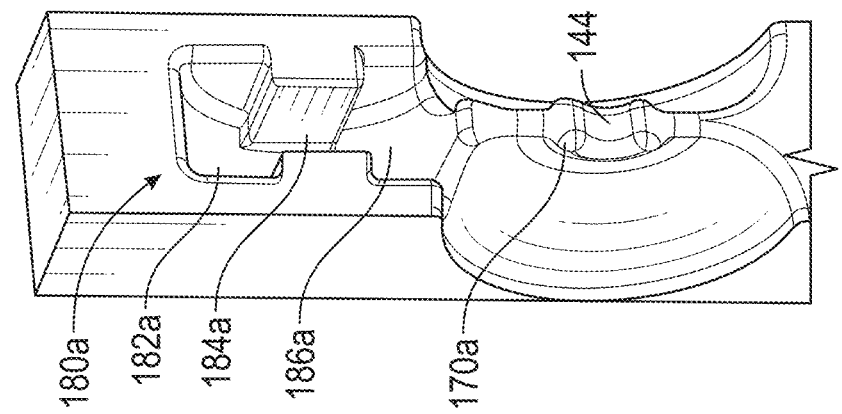
FIG. 17A shows an example side cell portion.

FIGS. 17A-17C show portions of a linac each having both an iris nose portion 170a and a side cell portion 180a. Particle accelerators, including split-structure particle accelerators, may include noses and/or side cells (e.g., side coupling cells) to improve performance. For example, side cells 180 may be included to improve frequency stability. One or more side cells 180 may include corresponding side cell portions 180a, 108b. FIG. 17A shows an example side cell portion 180a. The side cell portion 180a may include one or more sections, such as a distal portion 182a, a medial portion 184a, and/or a proximal portion 186a. The medial portion 184a may be disposed between the distal portion 182a and the proximal portion 186a. The terms distal, proximal, and medial may refer to a distance from the iris aperture 144. The side cell length 188 may be as shown in FIG. 17B. However, each of the portions of the side cell portion 180a may have a corresponding length. For example, the medial portion 184a may have a length that is smaller than one or both of a corresponding length of the distal portion 182a and/or the proximal portion 186a. A transition between distal portion 182a and medial portion 184a and/or between medial portion 184a and proximal portion 186a may be relatively sudden (e.g., as shown in FIG. 17A). This may be referred to as a "rectangular" coupling cell. However, in other embodiments, the transition is more gradual (e.g., in FIG. 17B or 17C). The transition may be referred to as a blend or blend radius.

The side cell length 188 may be between about 0.5 mm and 5.5 cm, between about 1 mm and 6 mm, and in some embodiments is about 2 mm or 3 mm (depending on the cell type). The medial portion 184a may have a length that is less than these values or within those ranges.

Figure 18:
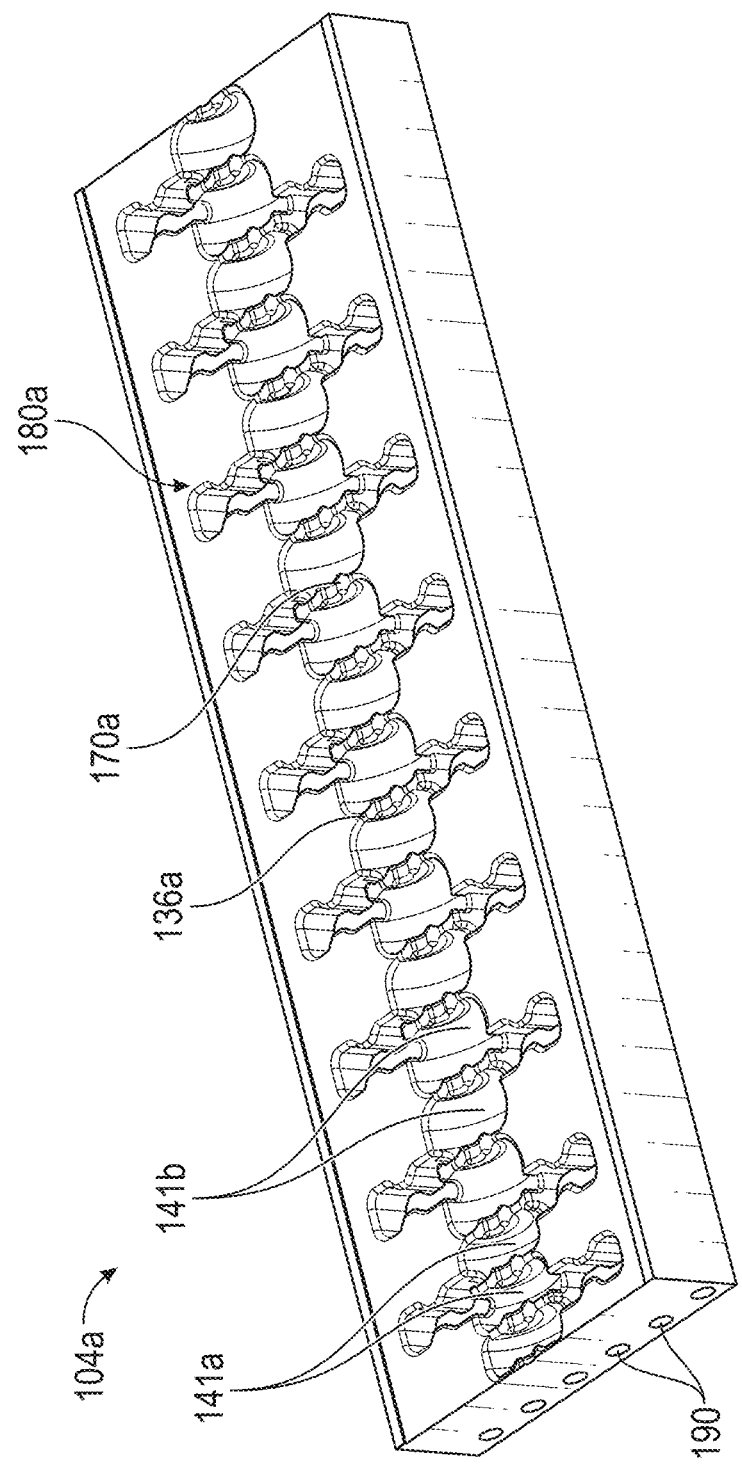
FIG. 18 shows an example of a split linac portion having a plurality of side cell portions.

FIG. 18 shows an example of a split linac portion 104a having a plurality of side cell portions 180a. The split linac portion 104a may include one or more types of cells, such as the first cell type 141a and second cell type 141b shown. The first cell type 141a may be referred to as "bunching cells." The bunching cells may be configured to accelerate particles at higher than 0.30. The bunching cells may have a shorter period and/or smaller blend radius than accelerating cells of a different type. For example, the blend radius of the bunching cells may be 2.5 mm while other accelerating cells 140 may have a higher radius (e.g., 5 mm or other value disclosed herein). Additional types of accelerating cells 140 may be included (see, e.g., FIG. 4). The side cell portions 180a may be axially offset from the accelerating cells 140 (e.g., first cell type 141a, second cell type 141b, etc.). The inclusion of side cells 180 may reduce the Q-factor relative to particle accelerators not having side cells. Q-factor can represent a ratio of stored energy multiplied by an angular frequency in oscillating fields to ohmic losses. The Q-factor may refer to a quality of how much a resonator is damped. For example, a higher Q-factor may result in longer lasting oscillations. The inclusion of one or more side cells 180 may be referred to as a side-coupled structure or an open side-coupled structure (OSCL).

One or more cooling channels may be included in the split linac 104. For example, as shown in FIG. 18, a plurality of cooling channels 190 may be disposed in the split linac portion 104a. Additional cooling channels may be in the split linac portion 104b. The cooling channels 190 may be configured to guide fluid (e.g., water) through the split linac portion 104a. The cooling channels 190 may be oriented roughly along the length of the split linac portion 104a. For example, one or more of the cooling channels 190 may be disposed approximately parallel to the beam axis of the split linac 104. One or more of the cooling channels 190 may have a diameter of between about 0.5 mm and 12 mm. In some embodiments, the diameter is between about 2 mm and 8 mm, and in certain embodiments is about 5 mm. The cooling channels 190 may be configured to draw heat at between about 2 kW/m$^2$/K and 30 kW/m$^2$/K, and in some embodiments at about 15 kW/m$^2$/K. The split linac 104 may include 1, 2, 3, 4, 5, 6, 8, 10, 12, or more cooling channels 190.

Figure 19A:
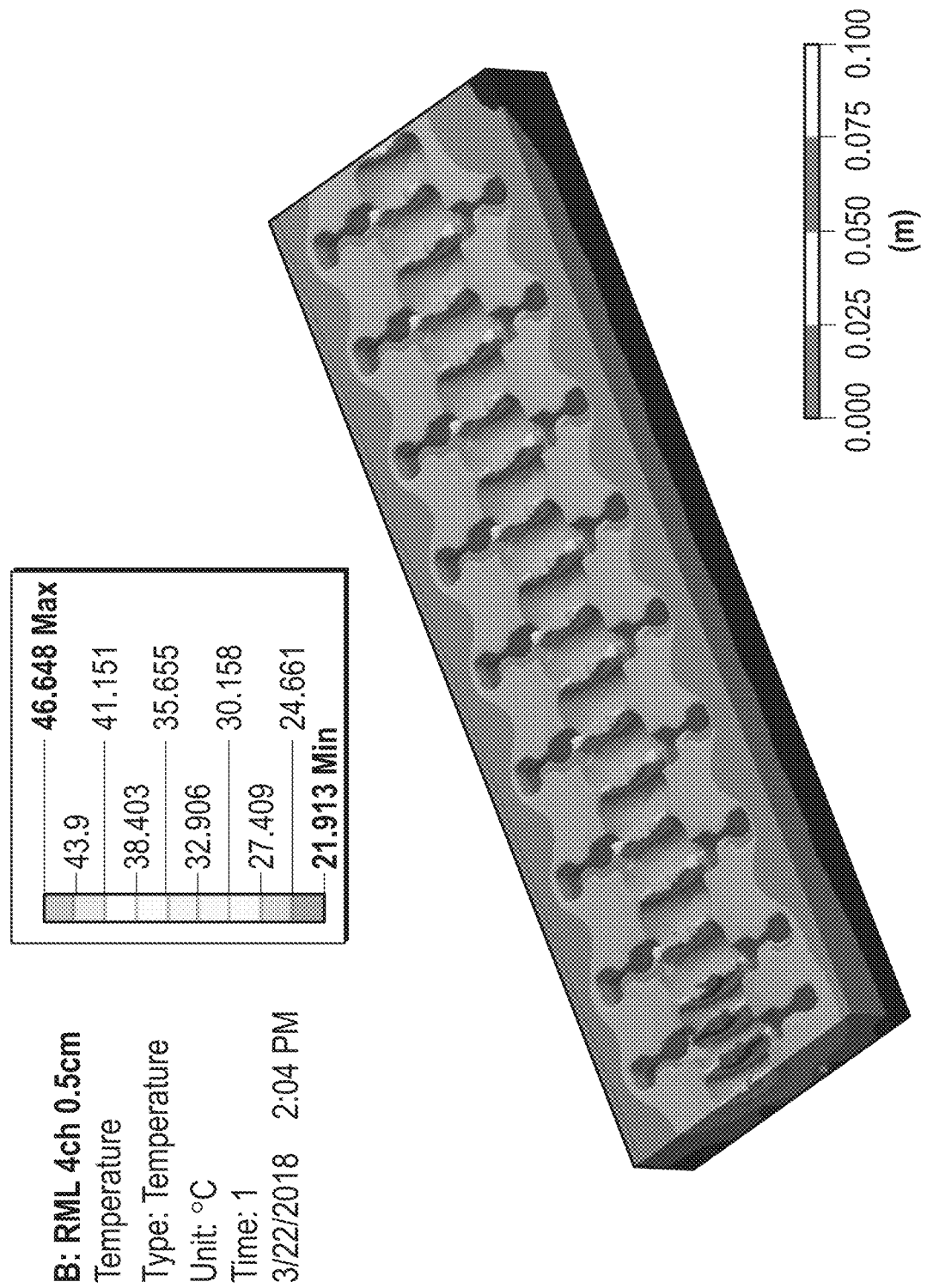
FIG. 19A shows an example heat map of a split linac having four cooling channels.
Figure 19B:
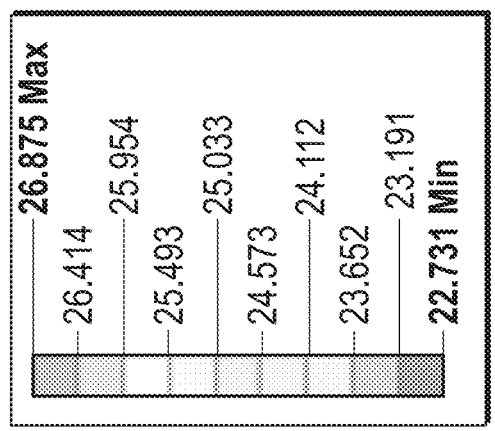
FIG. 19B shows an example heat map of a split linac having six cooling channels.
Figure 19B:
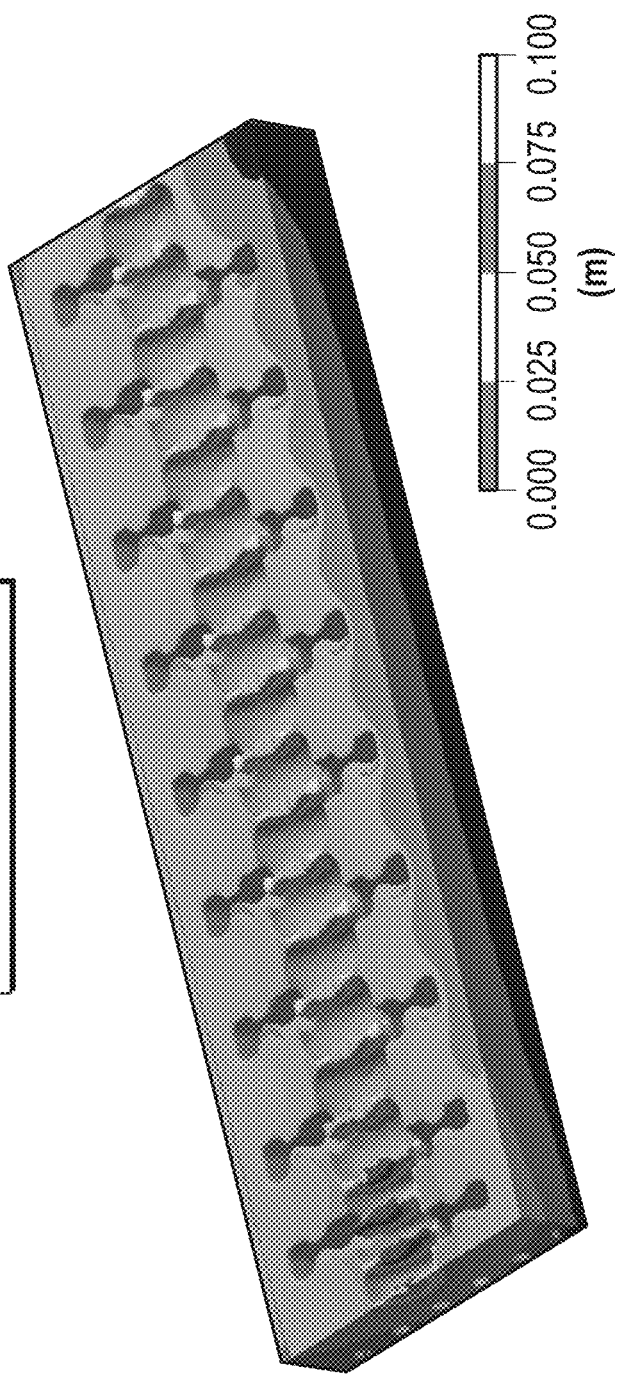
Figure 20:
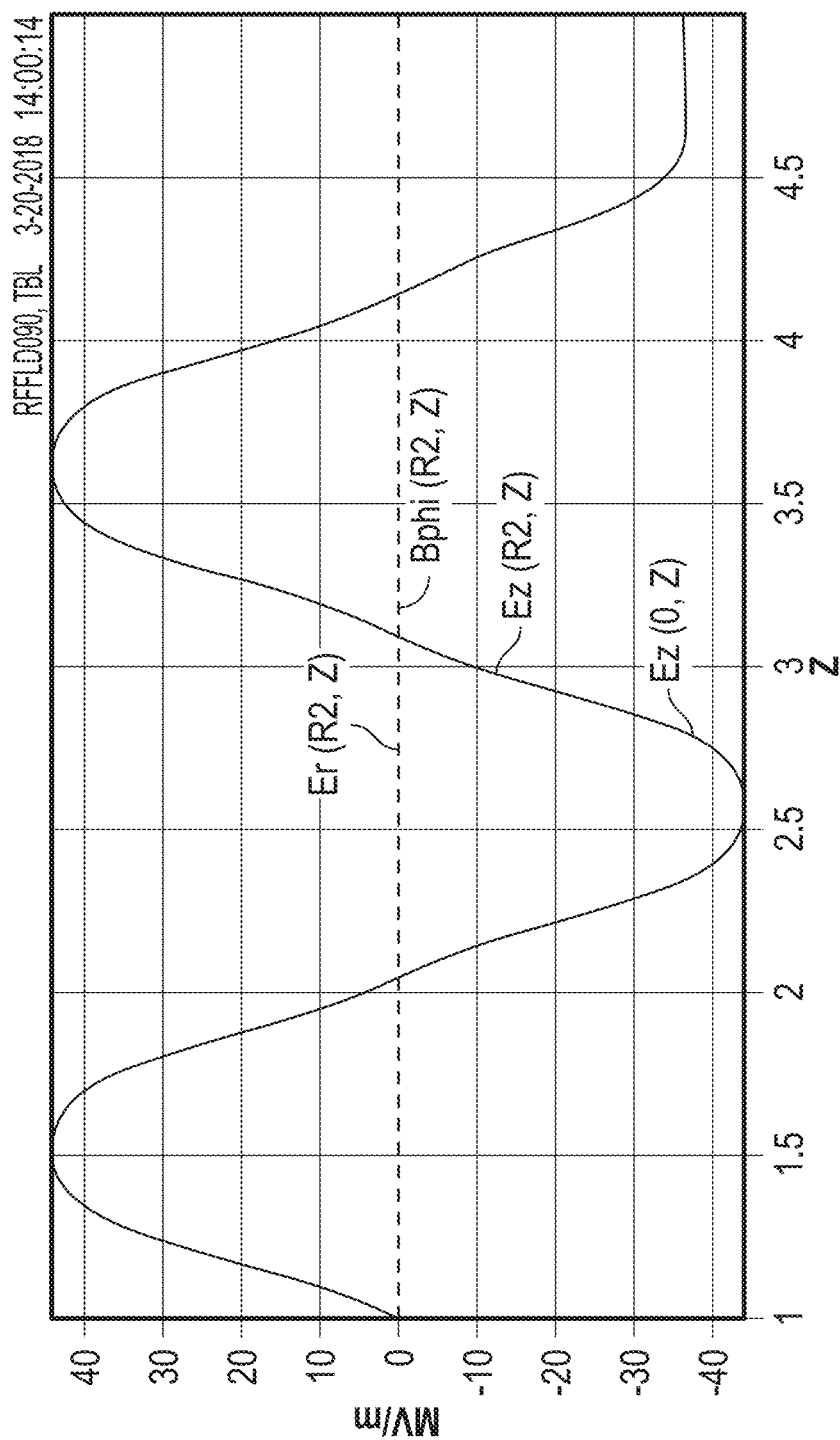
FIG. 20 shows an example acceleration gradient (in MV/m) along the beam path that may be achieved by a split linac described herein

FIG. 19A shows an example heat map of a split linac 104 having four cooling channels 190. FIG. 19B shows an example heat map of a split linac 104 having six cooling channels 190. Additional or fewer cooling channels 190 may be used. FIG. 20 shows an example acceleration gradient (in MV/m) along the beam path that may be achieved by a split linac 104 described herein.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended embodiments and/or claims and any equivalents thereof.

EXAMPLES

The following provides a list of examples of those described herein. This is a non-exhaustive and non-limiting list of examples.

In a 1st example, a linear accelerating structure for use in accelerating charged particles, the linear accelerating structure comprising: a first waveguide structure having a first substantially semi-cylindrical internal surface with a first plurality of ridges spaced apart along a first longitudinal axis of the first waveguide structure, each of the first plurality of ridges extending radially from the first substantially semi-cylindrical internal surface, wherein the first waveguide structure comprises a first bonding surface; and a second waveguide structure having a second substantially semi-cylindrical internal surface with a second plurality of ridges spaced apart along a second longitudinal axis of the second waveguide structure, each of the second plurality of ridges extending radially from the second substantially semi-cylindrical internal surface, wherein the second waveguide structure comprises a second bonding surface; wherein a first spacing between respective pairs of adjacent ridges of the first plurality of ridges along the first longitudinal axis is equal to a second spacing between a corresponding pair of adjacent ridges of the second plurality of ridges along the second longitudinal axis, and wherein the first bonding surface and the second bonding surface are configured to bind together to define a joined structure having a substantially cylindrical internal surface with corresponding ridges of the first and second plurality of ridges forming a plurality of accelerating cells each having a central aperture configured to allow a beam of charged particles to travel therethrough along a longitudinal axis extending through central apertures of each of the plurality of accelerating cells, the plurality of accelerating cells comprising an input coupling cell configured to receive electromagnetic waves from a magnetron; wherein at least one of the plurality of accelerating cells is configured to accelerate the beam of charged particles to a velocity between 0.1 and 1.0 times the speed of light; and wherein the joined structure is configured to propagate electromagnetic waves at a frequency greater than 1.0 GHz.

In a 2nd example, the linear accelerator of example 1, wherein at least one of the plurality of accelerating cells comprises an output coupling cell configured to direct an output of electromagnetic waves having a frequency greater than 1.0 GHz out of the joined structure.

In a 3rd example, the linear accelerating structure of any of examples 1-2, wherein the joined structure comprises one or more of copper, stainless steel, aluminum, or niobium.

In a 4th example, the linear accelerating structure of any of examples 1-3, wherein the first and second longitudinal axes are coaxial in the joined structure.

In a 5th example, the linear accelerating structure of any of examples 1-4, wherein the plurality of accelerating cells is configured to operate a standing electromagnetic wave at an operation mode.

In a 6th example, the linear accelerating structure of examples 5, wherein the operation mode is such that the phase of the wave in adjacent cells differs by an amount between $\pi/2$ and $\pi$.

In a 7th example, the linear accelerating structure of any of examples 1-4, wherein the plurality of accelerating cells is configured to house a traveling electromagnetic wave at an operation mode. The linear accelerating structure of example 7 may operate at an operation mode such that the phase of the wave in adjacent cells differs by an amount between $\pi/2$ and $\pi$.

In an 8th example, the linear accelerating structure of any of examples 1-8, wherein the joined structure has a total length measured along a beam axis of less than 1.0 m.

In a 9th example, the linear accelerating structure of any of examples 1-9, further comprising an electromagnetic generator configured to generate electromagnetic waves at a frequency greater than 1.0 GHz.

In a 10th example, the linear accelerating structure of any of examples 1-10, further comprising a charged particle generator configured to accelerate charged particles along a beam axis.

In an 11th example, the linear accelerator of any of examples 1-11 wherein the joined structure is configured to provide an acceleration gradient greater than 1 MV/m.

In a 12th example, the linear accelerating structure of any of examples 1-12, wherein the plurality of accelerating cells comprises a first accelerating cell and a second accelerating cell, the first accelerating cell configured to accelerate the beam of charged particles at a first velocity and the second accelerating cell configured to accelerate the beam of charged particles at a second velocity different from the first velocity.

In a 13th example, the linear accelerating structure of any of examples 1-13, wherein a joint formed by attachment of the first and second waveguide structures comprises a weld.

In a 14th example, the linear accelerating structure of any of examples 1-13, wherein a joint formed by attachment of the first and second waveguide structures comprises a braze.

In a 15th example, the linear accelerating structure of any of examples 1-13, wherein a joint formed by attachment of the first and second waveguide structures comprises a diffusion bond.

In a 16th example, a waveguide for use in accelerating charged particles, the waveguide comprising: a first structure comprising a first plurality of recesses spaced along a first axis; and a second structure comprising a second plurality of recesses spaced along a second axis; wherein a spacing between two adjacent recesses of the first plurality of recesses along the first axis matches a spacing between two corresponding adjacent recesses of the second plurality of recesses along the second axis; and wherein the first structure and the second structure are joined such that the first and second plurality of recesses form a plurality of accelerating cells, the plurality of accelerating cells configured to accelerate a beam of charged particles along a beam axis at a velocity between 0.1 and 1.0 times the speed of light.

In a 17th example, the waveguide of example 17, wherein each of the first plurality of recesses of the first structure forms a shape of a half-disc or ellipsoid.

In an 18th example, the waveguide of example 18, wherein the half-disc is oriented perpendicular to the beam axis.

In a 19th example, the waveguide of any of examples 17-19, wherein the first structure comprises a plurality of ridges separating each adjacent recess of the first plurality of recesses, each of the plurality of ridges forming half of an aperture configured to allow the beam of charged particles to travel therethrough along the beam axis.

In a 20th example, a method of manufacturing a linear accelerator, the method comprising: providing a first waveguide structure comprising a first plurality of recesses spaced apart along a first longitudinal axis of the first waveguide structure, the first plurality of recesses each extending radially from the first longitudinal axis of the first waveguide structure, wherein the first waveguide structure comprises a first bonding surface; providing a second waveguide structure comprising a second plurality of recesses spaced apart along a second longitudinal axis of the second waveguide structure, the second plurality of recesses each extending radially from the second longitudinal axis of the second waveguide structure, wherein the second waveguide structure comprises a second bonding surface; aligning the first plurality of recesses with the second plurality of recesses; and joining the first waveguide structure to the second waveguide structure such that the first and second plurality of recesses forming a plurality of accelerating cells of a joint structure; wherein each of the plurality of accelerating cells has a central aperture configured to allow a beam of charged particles to travel therethrough along a longitudinal axis extending through central apertures of each of the plurality of accelerating cells, the plurality of accelerating cells configured to accelerate the beam of charged particles to a velocity less than the speed of light.

In a 21st example, the method of example 21, wherein joining the first waveguide structure to the second waveguide structure to form the joint structure comprises electron beam welding.

In a 22nd example, the method of example 21, wherein joining the first waveguide structure to the second waveguide structure to form the joint structure comprises brazing.

In a 23rd example, the method of example 21, wherein joining the first waveguide structure to the second waveguide structure to form the joint structure comprises diffusion bonding.

In a 24th example, the method of any of examples 21-24, wherein joining the first waveguide structure to the second waveguide structure to form the joint structure comprises supplying a joining metal.

In a 25th example, the method of example 25, wherein the joining metal comprises copper.

In a 26th example, the method of example 25, wherein the joining metal comprises stainless steel.

In a 27th example, the method of any of examples 21-27, further comprising the step of forming the first plurality of recesses in the first waveguide structure.

In a 28th example, the method of example 28, wherein forming the first plurality of recesses in the first waveguide structure comprises milling.

In a 29th example, the method of example 28, wherein forming the first plurality of recesses in the first waveguide structure comprises electrical discharge machining.

In a 30th example, the method of any of examples 21-30, wherein the plurality of accelerating cells comprising an input coupling cell configured to receive electromagnetic waves from a magnetron.

In a 31st example, a particle accelerator comprising: a first waveguide portion comprising: a first plurality of cell portions; a first iris portion disposed between two of the first plurality of cell portions, the first iris portion comprising a portion of an aperture, the aperture configured to be disposed about a beam axis; and a first bonding surface; and a second waveguide portion comprising: a second plurality of cell portions; a second iris portion disposed between two of the second plurality of cell portions, the second iris portion comprising a portion of an aperture, the aperture configured to be disposed about a beam axis; and a second bonding surface; wherein: the first bonding surface is disposed adjacent the second bonding surface, the first and second plurality of cell portions form a plurality of accelerating cells, and the first and second iris portions form an iris.

In a 32nd example, the particle accelerator of example 32, wherein the aperture is configured to allow a beam of charged particles to travel therethrough along the beam axis.

In a 33rd example, the particle accelerator of any of examples 32-33, wherein the beam axis extends through a center of each of the plurality of accelerating cells.

In a 34th example, the particle accelerator of any of examples 32-34, further comprising an input coupling cell configured to receive electromagnetic waves therethrough.

In a 35th example, the particle accelerator of any of examples 32-35, wherein at least one of the plurality of accelerating cells is configured to accelerate a beam of charged particles to a velocity between 0.1 and 1.0 times the speed of light; and In a 36th example, the particle accelerator of any of examples 32-36, wherein the particle accelerator is configured to propagate electromagnetic waves at a frequency greater than 1.0 GHz.

In a 37th example, the particle accelerator of any of examples 32-37, wherein the particle accelerator is configured to operate at a mode between $\pi/2$ and $\pi$.

In a 38th example, the particle accelerator of any of examples 32-38, wherein a joint formed by attachment of the first and second waveguide portions comprises a braze.

In a 39th example, the particle accelerator of any of examples 32-39, wherein the joined structure is configured to provide an acceleration gradient greater than 1 MV/m.

In a 40th example, a method of manufacturing a particle accelerator, the method comprising: providing a first waveguide structure comprising a first plurality of recesses disposed along a first longitudinal axis of the first waveguide structure, wherein the first waveguide structure comprises a first bonding surface; providing a second waveguide structure comprising a second plurality of recesses disposed along a second longitudinal axis of the second waveguide structure, wherein the second waveguide structure comprises a second bonding surface; aligning the first plurality of recesses with the second plurality of recesses; and joining the first waveguide structure to the second waveguide structure such that the first and second plurality of recesses form a plurality of accelerating cells of a joint structure; wherein each of the plurality of accelerating cells has a central aperture configured to allow a beam of charged particles to travel therethrough along a longitudinal axis extending through central apertures of each of the plurality of accelerating cells.

In a 41st example, the method of example 40, wherein joining the first waveguide structure to the second waveguide structure to form the joint structure comprises electron beam welding.

In a 42nd example, the method of any of examples 40 to 41, wherein joining the first waveguide structure to the second waveguide structure to form the joint structure comprises brazing.

In a 43rd example, the method of any of examples 40 to 42, wherein joining the first waveguide structure to the second waveguide structure to form the joint structure comprises diffusion bonding.

In a 44th example, the method of any of examples 40 to 43, wherein joining the first waveguide structure to the second waveguide structure to form the joint structure comprises supplying a joining metal.

In a 45th example, the method of any of examples 40 to 44, wherein the joining metal comprises copper.

In a 46th example, the method of any of examples 40 to 45, wherein the joining metal comprises stainless steel.

In a 47th example, the method of any of examples 40 to 46, further comprising the step of forming the first plurality of recesses in the first waveguide structure.

In a 48th example, the method of example 47, wherein forming the first plurality of recesses in the first waveguide structure comprises milling.

In a 49th example, the method of any of examples 47 or 48, wherein forming the first plurality of recesses in the first waveguide structure comprises electrical discharge machining.

In a 50th example, the method of any of examples 40 to 49, wherein the plurality of accelerating cells comprising an input coupling cell configured to receive electromagnetic waves from a magnetron.

In a 51st example, the method of any of examples 40 to 50, wherein the first waveguide structure further comprises a first plurality of side recesses and wherein the second waveguide structure further comprises a second plurality of side recesses.

In a 52nd example, the method of example 51, wherein at least one recess of the first plurality of side recesses is axially offset from a corresponding recess of the first plurality of recesses.

In a 53rd example, the method of any of examples 51 to 52, wherein the at least one recess of the first plurality of side recesses comprises: a proximal portion having a length; a distal portion having a length; and a medial portion having a length, the medial portion disposed between the proximal and distal portions; wherein the length of the medial portion is less than the length of the proximal portion.

In a 54th example, the method of any of examples 40 to 53, wherein at least one of the plurality of accelerating cells comprises a nose.

In a 55th example, the method of example 54, wherein the nose comprises an increased thickness of a portion of the joint structure between neighboring cells of the first plurality of cells, the increased thickness being relative to one or more regions surrounding the nose of the portion of the joint structure.

In a 56th example, the method of any of examples 54 to 55, wherein the nose is configured to increase shunt impedance of a corresponding accelerating cell or plurality of corresponding accelerating cells of the joint structure.

In a 57th example, the method of any of examples 40 to 56, further comprising forming one or more channels within the joint structure configured to pass fluid therethrough, the one or more channels not intersecting with any of the plurality of accelerating cells.

In a 58th example, the method of example 57, wherein at least one of the one or more channels is disposed substantially parallel to beam axis.

In a 59th example, a particle accelerator comprising: a first waveguide portion comprising: a first plurality of cell portions; a first iris portion disposed between two of the first plurality of cell portions, the first iris portion comprising a first portion of an aperture; and a first bonding surface; and a second waveguide portion comprising: a second plurality of cell portions; a second iris portion disposed between two of the second plurality of cell portions, the second iris portion comprising a second portion of the aperture; and a second bonding surface; wherein: the first bonding surface is disposed adjacent the second bonding surface, the first and second plurality of cell portions form a plurality of accelerating cells, and the first and second iris portions form an iris and the aperture, the aperture configured to be disposed about a beam axis.

In a 60th example, the particle accelerator of example 59, wherein the aperture is configured to allow a beam of charged particles to travel therethrough along the beam axis.

In a 61st example, the particle accelerator of any of examples 59 to 60, wherein the beam axis extends through a center of each of the plurality of accelerating cells.

In a 62nd example, the particle accelerator of any of examples 59 to 61, further comprising an input coupling cell configured to receive electromagnetic waves therethrough.

In a 63rd example, the particle accelerator of any of examples 59 to 62, wherein at least one of the plurality of accelerating cells is configured to accelerate a beam of charged particles to a velocity between 0.1 and 1.0 times the speed of light.

In a 64th example, the particle accelerator of any of examples 59 to 63, wherein the particle accelerator is configured to propagate electromagnetic waves at a frequency greater than 1.0 GHz.

In a 65th example, the particle accelerator of any of examples 59 to 64, wherein the particle accelerator is configured to operate at a mode between $\pi/2$ and $\pi$.

In a 66th example, the particle accelerator of any of examples 59 to 65, wherein a joint formed by attachment of the first and second waveguide portions comprises a braze.

In a 67th example, the particle accelerator of any of examples 59 to 66, wherein the joined structure is configured to provide an acceleration gradient greater than 1 MV/m.

In a 68th example, the particle accelerator of any of examples 59 to 67, wherein the first waveguide portion further comprises a first plurality of side cell portions and wherein the second waveguide portion further comprises a second plurality of side cell portions.

In a 69th example, the particle accelerator of example 68, wherein at least one cell portion of the first plurality of side cell portions is axially offset from a corresponding cell portion of the first plurality of cell portions.

In a 70th example, the particle accelerator of any of examples 68 to 69, wherein the at least one cell portion of the first plurality of side cell portions comprises: a proximal portion having a length; a distal portion having a length; and a medial portion having a length, the medial portion disposed between the proximal and distal portions; wherein the length of the medial portion is less than the length of the proximal portion.

In a 71st example, the particle accelerator of any of examples 59 to 70, wherein at least one of the plurality of accelerating cells comprises a nose.

In a 72nd example, the particle accelerator of example 71, wherein the nose comprises an increased thickness of a portion of the joint structure between neighboring cells of the first plurality of cells, the increased thickness being relative to one or more regions surrounding the nose of the portion of the joint structure.

In a 73rd example, the particle accelerator of any of examples 71 to 72, wherein the nose is configured to increase shunt impedance of a corresponding accelerating cell or plurality of corresponding accelerating cells of the joint structure.

In a 74th example, the particle accelerator of any of examples 59 to 73, further comprising forming one or more channels within the joint structure configured to pass fluid therethrough, the one or more channels not intersecting with any of the plurality of accelerating cells.

In a 75th example, the particle accelerator of example 74, wherein at least one of the one or more channels is disposed substantially parallel to beam axis.

What is claimed is:

1. A method of manufacturing a particle accelerator, the method comprising:
   providing a first waveguide structure comprising:
      a first plurality of accelerating recesses disposed along a first longitudinal axis of the first waveguide structure;
      a first plurality of side recesses each disposed off-axis from one or more of the first plurality of accelerating recesses; and
      a first raised outer section forming a first recessed inner section surrounding the first plurality of accelerating recesses and the first plurality of side recesses;
   providing a second waveguide structure comprising:
      a second plurality of accelerating recesses;

a second plurality of side recesses each disposed off-axis from one or more of the second plurality of accelerating recesses; and
a second raised outer section forming a second recessed inner section surrounding the second plurality of accelerating recesses and the second plurality of side recesses;
aligning the first pluralities of accelerating and side recesses with corresponding recesses of the second pluralities of accelerating and side recesses; and
joining the first waveguide structure to the second waveguide structure at the first and second raised outer sections such that the first and second pluralities of accelerating and side recesses form a plurality of accelerating cells and side cells of a joint structure.

2. The method of claim 1, wherein joining the first waveguide structure to the second waveguide structure to form the joint structure comprises electron beam welding.

3. The method of claim 1, wherein joining the first waveguide structure to the second waveguide structure to form the joint structure comprises brazing.

4. The method of claim 1, wherein joining the first waveguide structure to the second waveguide structure to form the joint structure comprises diffusion bonding.

5. The method of claim 1, wherein joining the first waveguide structure to the second waveguide structure to form the joint structure comprises supplying a joining metal.

6. The method of claim 1, further comprising disposing a particle source to abut the joint structure.

7. The method of claim 1, further comprising milling the first plurality of accelerating recesses into the first waveguide structure.

8. The method of claim 1, further comprising electrical discharge machining at least a portion of the first waveguide structure.

9. The method of claim 1, wherein each of the plurality of accelerating cells has a central aperture configured to allow a beam of charged particles to travel therethrough along a longitudinal axis extending through central apertures of each of the plurality of accelerating cells.

10. The method of claim 1, wherein at least one recess of the first plurality of side recesses is axially offset from a corresponding recess of the first plurality of accelerating recesses.

11. A particle accelerator comprising:
a first waveguide portion comprising:
a first plurality of accelerating cell portions;
a first plurality of side cell portions; and
a first raised outer section forming a first recessed inner section surrounding the first plurality of accelerating cell portions and the first plurality of side cell portions;
and
a second waveguide portion comprising:
a second plurality of accelerating cell portions;
a second plurality of side cell portions; and
a second raised outer section forming a second recessed inner section surrounding the second plurality of accelerating cell portions and the second plurality of side cell portions;
wherein:
the first raised outer section is disposed adjacent the second raised outer section along corresponding bonding surfaces, and
the first and second pluralities of accelerating cell portions form a plurality of accelerating cells of a joint structure.

12. The particle accelerator of claim 11, wherein the first waveguide comprises an aperture configured to allow a beam of charged particles to travel therethrough along a beam axis.

13. The particle accelerator of claim 11, further comprising a particle source configured to abut the joint structure.

14. The particle accelerator of claim 11, further comprising an input coupling cell configured to receive electromagnetic waves therethrough.

15. The particle accelerator of claim 11, wherein the particle accelerator is configured to operate at a mode between $\pi/2$ and $\pi$.

16. The particle accelerator of claim 11, wherein each of the plurality of accelerating cells comprises a corresponding iris and aperture, each aperture configured to be disposed about a beam axis.

17. The particle accelerator of claim 11, wherein at least one cell portion of the first plurality of side cell portions is axially offset from a corresponding cell portion of the first plurality of cell portions.

18. The particle accelerator of claim 17, wherein the at least one cell portion of the first plurality of side cell portions comprises:
a proximal portion having a length;
a distal portion having a length; and
a medial portion having a length, the medial portion disposed between the proximal and distal portions;
wherein the length of the medial portion is less than the length of the proximal portion.

19. The particle accelerator of claim 11, wherein at least one of the plurality of accelerating cells comprises a nose.

20. The particle accelerator of claim 19, wherein the nose comprises an increased thickness of a portion of the joint structure between neighboring cells of the first plurality of cells, the increased thickness being relative to one or more regions surrounding the nose of the portion of the joint structure.

* * * * *